(12) United States Patent
Dörrwächter et al.

(10) Patent No.: US 11,124,488 B2
(45) Date of Patent: Sep. 21, 2021

(54) PREPARATION OF 2-([1,2,3]TRIAZOL-2-YL)-BENZOIC ACID DERIVATIVES

(71) Applicant: IDORSIA PHARMACEUTICALS LTD, Allschwil (CH)

(72) Inventors: Patric Dörrwächter, Allschwil (CH); Gunther Schmidt, Allschwil (CH)

(73) Assignee: Idorsia Pharmaceuticals Ltd, Allschwil (CH)

( * ) Notice: Subject to any disclaimer, the term of this patent is extended or adjusted under 35 U.S.C. 154(b) by 47 days.

(21) Appl. No.: 16/610,413

(22) PCT Filed: May 2, 2018

(86) PCT No.: PCT/EP2018/061172
§ 371 (c)(1),
(2) Date: Nov. 1, 2019

(87) PCT Pub. No.: WO2018/202689
PCT Pub. Date: Nov. 8, 2018

(65) Prior Publication Data
US 2021/0114997 A1   Apr. 22, 2021

(30) Foreign Application Priority Data

May 3, 2017   (WO) ................. PCT/EP2017/060451

(51) Int. Cl.
*C07D 249/06* (2006.01)

(52) U.S. Cl.
CPC ........ *C07D 249/06* (2013.01); *C07B 2200/13* (2013.01)

(58) Field of Classification Search
CPC .................................................. C07D 249/06
See application file for complete search history.

(56) References Cited

U.S. PATENT DOCUMENTS

| | | | |
|---|---|---|---|
| 7,994,336 B2 | 8/2011 | Aissaoui et al. |
| 8,288,435 B2 | 10/2012 | Aissaoui et al. |
| 9,150,566 B2 | 10/2015 | Bolli et al. |
| 9,403,813 B2 | 8/2016 | Bolli et al. |
| 9,493,446 B2 | 11/2016 | Bolli et al. |
| 9,732,075 B2 | 8/2017 | Boss et al. |
| 9,790,208 B2 | 10/2017 | Boss et al. |
| 9,914,720 B2 | 3/2018 | Boss et al. |
| 9,914,721 B2 | 3/2018 | Boss et al. |
| 10,023,560 B2 | 7/2018 | Boss et al. |
| 10,329,287 B2 | 6/2019 | Boss et al. |
| 2010/0016401 A1 | 1/2010 | Aissaoui et al. |
| 2010/0222328 A1 | 9/2010 | Aissaoui et al. |
| 2012/0202783 A1 | 8/2012 | Branstetter et al. |
| 2012/0208812 A1 | 8/2012 | Chai et al. |
| 2013/0137672 A1 | 5/2013 | Branstetter et al. |
| 2013/0281465 A1 | 10/2013 | Nozawa et al. |
| 2014/0171430 A1 | 6/2014 | Letavic et al. |
| 2014/0228377 A1 | 8/2014 | Abe et al. |
| 2014/0275065 A1 | 9/2014 | Coate et al. |
| 2014/0275095 A1 | 9/2014 | Dvorak et al. |
| 2015/0166527 A1 | 6/2015 | Boss et al. |
| 2015/0252032 A1 | 9/2015 | Bolli et al. |
| 2016/0024064 A1 | 1/2016 | Bolli et al. |
| 2016/0046640 A1 | 2/2016 | Coate et al. |
| 2016/0355506 A1 | 12/2016 | Boss et al. |
| 2016/0368901 A1 | 12/2016 | Boss et al. |
| 2017/0001985 A1 | 1/2017 | Boss et al. |
| 2017/0305897 A1 | 10/2017 | Boss et al. |
| 2018/0002317 A1 | 1/2018 | Boss et al. |

FOREIGN PATENT DOCUMENTS

| | | |
|---|---|---|
| CN | 104649983 | 5/2015 |
| JP | 2014/015452 | 1/2014 |
| WO | WO 2008/020405 | 2/2008 |

(Continued)

OTHER PUBLICATIONS

"Perry's Chemical Engineers' Handbook—Seventh Edition," 2641 pages (1997).

(Continued)

*Primary Examiner* — Shawquia Jackson
(74) *Attorney, Agent, or Firm* — Hoxie & Associates LLC

(57) ABSTRACT

The present invention relates to a process for the preparation of particular 2-(2H-[1,2,3]triazol-2-yl)-benzoic acid derivatives of formula (I)

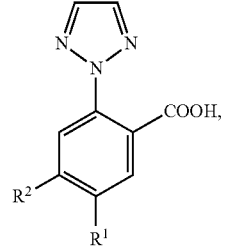

Formula (I)

to certain crystalline forms of potassium salts of said 2-(2H-[1,2,3]triazol-2-yl)-benzoic acid derivatives of formula ($I_K$), to certain crystalline forms of said 2-(2H-[1,2,3]triazol-2-yl)-benzoic acid derivatives of formula (I), and to their use in the preparation of pharmaceuticals such as (S)-(2-(5-chloro-4-methyl-1H-benzo[d]imidazol-2-yl)-2-methylpyrrolidin-1-yl)-(5-methoxy-2-(2H-1,2,3-triazol-2-yl)phenyl)methanone.

51 Claims, 5 Drawing Sheets

(56) References Cited

FOREIGN PATENT DOCUMENTS

| WO | WO 2008/038251 | 4/2008 |
|---|---|---|
| WO | WO 2008/081399 | 7/2008 |
| WO | WO 2008/139416 | 11/2008 |
| WO | WO 2008/150364 | 12/2008 |
| WO | WO 2011/050198 | 4/2011 |
| WO | WO 2011/050200 | 4/2011 |
| WO | WO 2011/050202 | 4/2011 |
| WO | WO 2012/081692 | 6/2012 |
| WO | WO 2012/085852 | 6/2012 |
| WO | WO 2012/085857 | 6/2012 |
| WO | WO 2012/145581 | 10/2012 |
| WO | WO 2012/148553 | 11/2012 |
| WO | WO 2013/005755 | 1/2013 |
| WO | WO 2013/050938 | 4/2013 |
| WO | WO 2013/068935 | 5/2013 |
| WO | WO 2013/169610 | 11/2013 |
| WO | WO 2013/182972 | 12/2013 |
| WO | WO 2014/057435 | 4/2014 |
| WO | WO 2014/141065 | 9/2014 |
| WO | WO 2014/159591 | 10/2014 |
| WO | WO 2014/165065 | 10/2014 |
| WO | WO 2015/083070 | 6/2015 |
| WO | WO 2015/083071 | 6/2015 |
| WO | WO 2015/083094 | 6/2015 |
| WO | WO 2016/020403 | 2/2016 |

OTHER PUBLICATIONS

Baxter, C.A., et al., "The First Large-Scale Synthesis of MK-4305: A Dual Orexin Receptor Antagonist for the Treatment of Sleep Disorder," *Org. Process Res. Dev.*, vol. 15: 367-375 (2011).

Coleman, P.J, et al., "Discovery of Dual Orexin Receptor Antagonists (DORAs) for the Treatment of Insomnia," *Current Topics in Medicinal Chemistry*, vol. 11: 696-725 (2011).

Cox, C.D., et al., "Discovery of the Dual Orexin Receptor Antagonist [(7R)-4-(5-Chloro-1,3-benzoxazol-2-yl)-7-methyl-1,4-diazepan-1-yl][5-methyl-2-(2H-1,2,3-triazol-2-yl)phenyl]methanone (MK-4305) for the Treatment of Insomnia," *J. Med. Chem.*, vol. 53: 5320-5332 (2010).

Griesser, U.J. et al., "The Important of Solvates," *Polymorphism in the Pharmaceutical Industry—1st Edition*, Chapter 8, 19 pages (2006).

Wang, X-J et al., "General Solution to the Synthesis of N-2-Substituted 1,2,3-Triazoles," *Organic Letters*, vol. 12(20): 4632-4635 (2010).

PREPARATION OF 2-([1,2,3]TRIAZOL-2-YL)-BENZOIC ACID DERIVATIVES

CROSS REFERENCE TO RELATED APPLICATIONS

This application is a United States Application under 35 U.S.C. 371 claiming benefit of PCT Application No. PCT/EP2018/061172, filed on May 2, 2018, which claims the benefit of PCT Application No. PCT/EP2017/060451, filed on May 3, 2017, the contents of which are incorporated herein by reference.

The present invention relates to a process for the preparation of particular 2-(2H-[1,2,3]triazol-2-yl)-benzoic acid derivatives of formula (I), to certain crystalline forms of potassium salts of said 2-(2H-[1,2,3]triazol-2-yl)-benzoic acid derivatives of formula ($I_K$), to certain crystalline forms of said 2-(2H-[1,2,3]triazol-2-yl)-benzoic acid derivatives of formula (I), and to their use in the preparation of pharmaceuticals, especially certain orexin receptor antagonists such as (S)-(2-(5-chloro-4-methyl-1H-benzo[d]imidazol-2-yl)-2-methylpyrrolidin-1-yl)-(5-methoxy-2-(2H-1,2,3-triazol-2-yl)phenyl)methanone.

Orexin receptor antagonists comprising 2-(2H-[1,2,3]triazol-2-yl)-benzoic acid moieties are known for example from WO2008/020405; WO2008/038251; WO2008/081399; WO2008/139416, WO2008/150364, WO2011/050200, WO2012/148553, WO2013/068935, WO2013/169610, WO2013/182972, WO2014/057435, WO2104/141065, WO2015/083071, WO2015/083070, WO2015/083094, WO2016/020403, J. Med. Chem. 2010, 53, 5320-5332, Current Topics in Medicinal Chemistry, 2011, 11, 696-725.

Usual conditions for the preparation of 2-(2H-[1,2,3]triazol-2-yl)-benzoic acid derivatives comprise a coupling reaction of the corresponding 2-iodo-benzoic acid derivative with 1H-[1,2,3]triazole in presence of $Cs_2CO_3$ and copper (I) iodide (CuI) in a high boiling solvent (DMF) at elevated temperatures/under microwave conditions. The purification procedures generally use a sequence of i) extraction of the mixture of regioisomers from the acidified reaction mixture, and ii) removal of the wrong regioisomer by slurrying in EtOAc, or by crystallization from EtOAc, and/or by flash chromatography/preparative HPLC, thus, conditions generally not amenable to large scale industrial production.

For example WO2015/083071, WO2015/083070 and WO2015/083094 disclose that 5-methoxy-2-(2H-[1,2,3]triazol-2-yl)-benzoic acid:

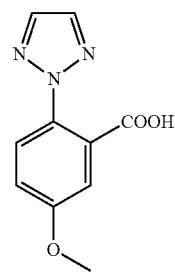 [SMILES: COc1ccc(-n2nccn2)c(C(=O)O)c1]

is obtained without using flash chromatography or preparative HPLC, but containing 6% of the triazole N1-regioisomer as impurity.

WO2011/050200 discloses an approach for the synthesis of the regioisomeric compound 4-methoxy-2-(2H-[1,2,3]triazol-2-yl-benzoic acid (Intermediate 49):

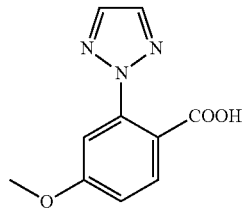 [SMILES: COc1ccc(C(=O)O)c(-n2nccn2)c1]

starting from the corresponding 2-bromo-benzoic acid derivative: 2-bromo-4-methoxy-benzoic acid using $Cs_2CO_3$/CuI/(1R,2R)—N1,N2-dimethylcyclohexan-1,2-diamine in dioxane at 100° C. Purification was similar to the usual conditions described before. WO2011/050200 also discloses the regioisomeric compound 5-methoxy-2-(2H-[1,2,3]triazol-2-yl-benzoic acid (Intermediate 61) and the compound 5-methyl-2-(2H-[1,2,3]triazol-2-yl-benzoic acid (Intermediate 59), which were prepared from the corresponding iodobenzoic acid using the above-described usual conditions.

WO2013/068935 discloses the synthesis of several 2-(2H-[1,2,3]triazol-2-yl)-benzoic acid derivatives including the compound 4-methyl-2-(2H-[1,2,3]triazol-2-yl-benzoic acid (Intermediate E-4):

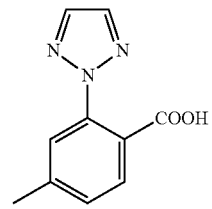

starting from the corresponding iodo-benzoic acid derivatives.

Further to the medicinal chemistry procedures disclosed in some of the above references, certain processes amenable to large scale industrial production have been published. For example WO2013/169610 and C. A. Baxter et al. (Organic Process Research & Development 2011, 15, 367-375 disclose large scale processes relating to suvorexant (MK-4305). The 2-([1,2,3]triazol-2-yl)-benzoic acid derivative 5 is prepared starting from the corresponding iodide 19.

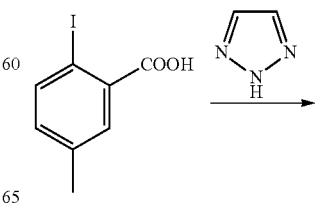

19

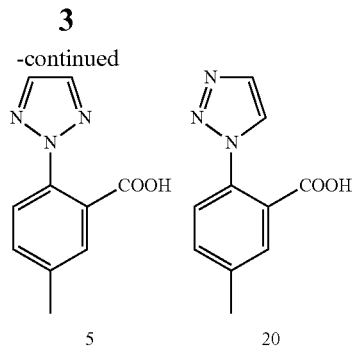

Under optimized conditions using CuI/K$_2$CO$_3$ in THF/DMF at 65° C. a 81:19 ratio of regioisomers 5/20 was formed. It is stated in Baxter et al. that "attempts to reject the regioisomer 20 by crystallization under a number of conditions was not successful due to the lower solubility of this compound compared to that of 5. On this basis purification via salt formation was explored. The cesium and potassium salts did not give significant upgrades; however, formation of the sodium salt in THF with adjustment of solvent volume led to the undesired isomer being rejected at the expense of around 15% of the desired isomer."

The detailed purification procedures use a sequence of i) extraction of the mixture of regioisomers from the acidified reaction mixture, ii) sodium salt formation using sodium tert.-butoxide in THF, crystallization and filtration, iii) salt breaking and crystallization, and iv) recrystallization to yield (Baxter et al.) 60% of 5 with a melting point of 174-176° C. (167.5° C. in WO2013/169610).

The present invention provides a novel process for the preparation of certain 2-(2H-[1,2,3]triazol-2-yl)-benzoic acid derivatives of Formula (I) from the respective bromo-benzoic acid precursor which is in general less cost-intensive and, thus, more readliy available than the corresponding iodo-derivative. The process uses a direct solid-liquid separation e.g. by precipitation of the respective 2-(2H-[1,2,3] triazol-2-yl)-benzoic acid potassium salt of Formula (I$_K$) from the reaction mixture, thus, leading in a shortened process to crystalline and regioisomerically enriched 2-(2H-[1,2,3]triazol-2-yl)-benzoic acid potassium salts. The crystalline potassium salts are novel, and, after salt break, lead to novel crystalline forms of 2-(2H-[1,2,3]triazol-2-yl)-benzoic acid derivatives of Formula (I), which are regioisomerically essentially pure, and may serve as valuable intermediates in the synthesis of certain orexin recptor antagonists. The present process, thus, reduces the number of steps necessary to obtain crystalline and regioisomerically essentially pure crystalline 2-(2H-[1,2,3]triazol-2-yl)-benzoic acid derivatives of Formula (I), and may be amenable to an efficient large scale synthesis of pharmaceutically active compounds.

DESCRIPTION OF THE FIGURES

FIG. 3 in addition shows peaks attributable to an KHCO$_3$ impurity at 12.1° (6%), 24.1° (5%), 30.1° (36%), 31.3° (52%), 31.8° (11%), 34.1° (23%).

Figure 1:
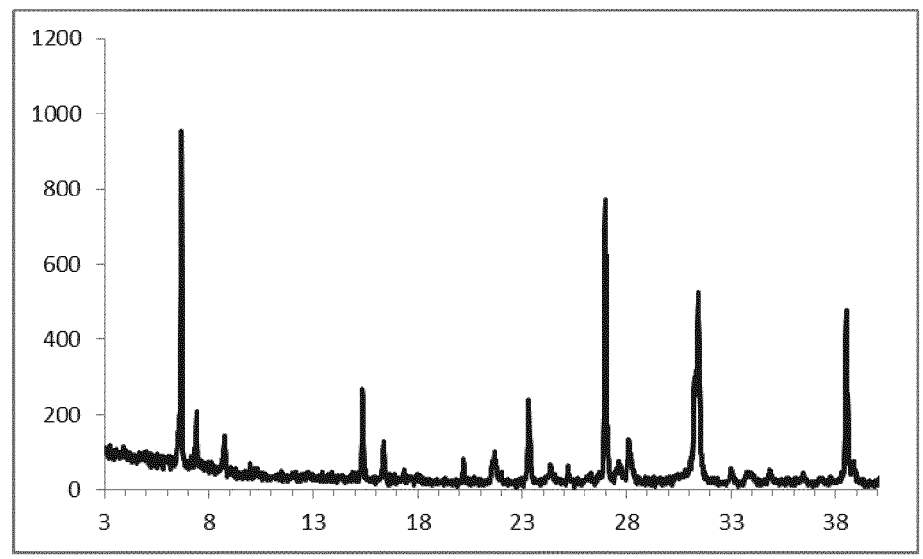
FIG. 1 shows the X-ray powder diffraction diagram of crystalline 5-methoxy-2-(2H-[1,2,3]triazol-2-yl)-benzoic acid potassium salt, the compound of Example 1.1. The X-ray diffraction diagram shows peaks having a relative intensity, as compared to the most intense peak in the diagram, of the following percentages (relative peak intensitites given in parenthesis) at the indicated angles of refraction 2theta (selected peaks from the range 3-40° 2theta are reported): 6.7° (100%), 7.4° (24%), 8.7° (10%), 15.4° (43%), 16.4° (16%), 20.2° (10%), 21.7° (10%), 23.3° (18%), 24.4° (9%), 27.0° (87%), 28.10 (15%), 31.4° (85%).

For avoidance of any doubt, the above-listed peaks describe the experimental results of the X-ray powder diffraction shown in the above Figures. It is understood that, in contrast to the above peak list, only a selection of characteristic peaks is required to fully and unambiguously characterize of the respective compound/compound salt in the respective crystalline form of the present invention.

In the X-ray diffraction diagrams the angle of refraction 2theta (2θ) is plotted on the horizontal axis and the counts on the vertical axis.

DETAILED DESCRIPTION OF THE INVENTION

1) A first aspect of the invention relates to a process for the synthesis of a crystalline potassium salt of a 2-(2H-[1,2,3]triazol-2-yl)-benzoic acid derivative, a crystalline compound of Formula ($I_K$)

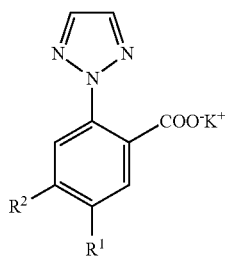

Formula ($I_K$)

wherein
$R^1$ represents methoxy and $R^2$ represents hydrogen; or
$R^1$ represents hydrogen and $R^2$ represents methyl;
said process comprising the coupling of
a compound of Formula (II):

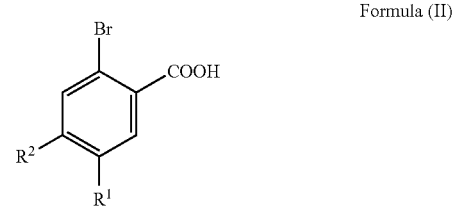

Formula (II)

and [1,2,3]triazole:

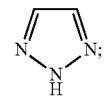

wherein said process is conducted in the presence of:
copper (I) iodide (CuI);
an inorganic potassium base (in particular $K_2CO_3$); and
a solvent or solvent mixture which is
a water miscible ether solvent (especially THF, 2-methyl-THF, dioxane, 1,2-dimethoxyethane); or
a polar aprotic solvent (especially DMF, dimethylacetamide, NMP);
or any mixture thereof;
wherein said solvent or solvent mixture is present in an amount of about 5 to 100 vol (notably about 10 to 50 vol, especially about 20 to 40 vol) with respect to the compound of Formula (II);
wherein said coupling of the compound of Formula (II) and [1,2,3]triazole is performed at a temperature of greater than about 60° C. (notably about 60° C.-120° C., especially about 80° C.-120° C., in particular about 90° C.-110° C.);
wherein said crystalline compound of Formula ($I_K$) is isolated from the reaction mixture by solid-liquid separation.

It is well understood that [1,2,3]triazole may be present in form of its tautomeric forms 1H-[1,2,3]triazole and 2H-[1,2,3]triazole, and both tautomeric forms are encompassed by the denomination [1,2,3]triazole.

The solvent or solvent mixture that may be used for the process according to embodiment 1) may especially be defined as consisting essentially of:
a water miscible ether solvent, especially a water miscible ether solvent having a boiling point of at least 60° C., such as in particular 1,4-dioxane; or 1,2-dimethoxyethane, tetrahydrofurane (THF), 2-methyl-tetrahydrofurane (2-Me-THF), or 4-methyl tetrahydropyran (4-Me-THP); or
a polar aprotic solvent, especially polar aprotic amide containing solvent, such as in particular dimethylformamide (DMF); or dimethylacetamide, N-methylpyrrolidin-2-one (NMP), or dimethylsulfoxide (DMSO); or
a mixture of more than one water miscible ether solvents; or a mixture of one or more water miscible ether solvent(s) with one or more polar aprotic solvent(s);
wherein said solvent or solvent mixture is present in an amount of about 5 to 100 vol (notably about 10 to 50 vol, especially about 20 to 40 vol) with respect to the compound of Formula (II)

A preferred example of such solvent or solvent mixture is the water miscible ether solvent 1,4-dioxane (dioxane).

The term "ether solvent" refers to a solvent consisting of a saturated straight chain or branched acyclic hydrocarbon group, or a saturated cyclic hydrocarbon group optionally mono-substituted with a straight chain or branched acyclic hydrocarbon group, wherein said acyclic hydrocarbon group or said cyclic hydrocarbon group contains at least one bivalently bound oxygen atom. The term "water miscible ether solvents" includes ether solvents which are partially water miscible. Partially water miscible ether solvents may be defined as ether solvents which are miscible with at least 1% wt/wt of water dissolved in the respective ether solvent (it being understood that if such solvent is partially miscible, it is not fully miscible with water at any ratio). Preferred water miscible ether solvents have a boiling point of at least 60° C. Examples of such ether solvents are the water miscible ether solvents 1,4-dioxane and 1,2-dimethoxy-ethane, as well as the partially miscible ether solvents tetrahydrofurane (THF), 2-methyl-tetrahydrofurane (2-Me-THF), and 4-methyl tetrahydropyran (4-Me-THP).

The term "polar aprotic solvents" refers especially to polar aprotic amide containing solvents such as dimethyl-formamide (DMF), dimethylacetamide, and N-methylpyr-rolidin-2-one (NMP). An example of "a mixture of one or more water miscible ether solvent(s) with one or more polar aprotic solvent(s)" is a mixture of THF and DMF, e.g. in a ratio v/v of about 4:1 to 10:1, especially in a ratio v/v of about 5:1. All solvents can be used as purchased without additional drying procedures.

It may be preferable the coupling reaction of the process of embodiment 1) is performed in a reaction mixture containing, in addition to the respective solvent, a certain amount of water, for example about 0.05 to 2 vol (notably about 0.1 to 1 vol) with respect to the compound of Formula (II). In case the respective solvent is a water miscible ether solvent, the ratio (v/v) of water miscible ether solvent to water is greater than about 10:1 (v/v), especially about 20:1 to 100:1 (v/v), in particular about 30:1 to 80:1 (v/v). For avoidance of any doubt, such additional water present in the reaction mixture is not considered a "solvent", or part of a "solvent mixture", as defined before.

Said process of embodiment 1) is performed in presence of an inorganic potassium base. Examples are especially $K_2CO_3$, as well as $K_3PO_4$ and $KHCO_3$.

Said process of embodiment 1) may be performed in presence of a ligand. Examples are 8-hydroxyquinoline, N1,N2-dimethylcyclohexan-1,2-diamine, and N,N-dimethyl-ethylene-diamine. In case a a polar aprotic solvent (especially polar aprotic amide containing solvent, such as in particular dimethylformamide (DMF)) or a mixture containing such solvent is used, said process of embodiment 1) is preferably performed in presence of a ligand as set out before.

Said process of embodiment 1) leads to the formation of the compounds of Formula (I) in regioisomerically enriched form as measured in the reaction mixture before isolation (especially the regioisomeric ratio is greater than 70:30). Isolation of the crystalline compound of Formula $(I_K)$ from the reaction mixture by solid-liquid separation according to embodiment 1) leads to the crystalline potassium salt in regioisomerically further enriched form, and may lead to the crystalline potassium salt in regioisomerically essentially pure form (especially in a regioisomeric ratio of greater than about 80:20 (especially greater than about 85:15, in particular greater than about 90:10).

2) Another embodiment, thus, relates to the process according to embodiment 1), wherein the regioisomeric ratio of the crystalline compound of Formula $(I_K)$ obtained from said solid-liquid separation; i.e. the ratio of [compound of Formula $(I_K)$]: [compound of Formula $(I_{R-K})$]:

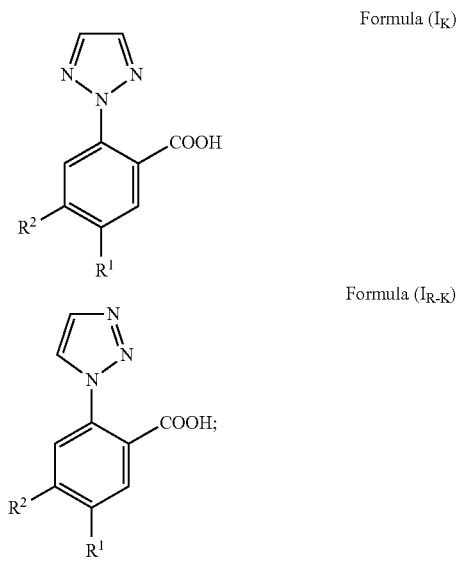

is greater than about 80:20 (especially greater than about 85:15, in particular greater than about 90:10).

3) Another embodiment relates to the process according to embodiments 1) or 2), wherein said process is conducted in the presence of Cu (I) iodide (CuI); wherein Cu (I) iodide is present in an amount of about 0.01 eq. to 0.5 eq. (notably about 0.01 eq. to 0.1 eq.; especially about 0.05 eq.) with respect to the compound of Formula (II).

4) Another embodiment relates to the process according to any one of embodiments 1) to 3), wherein said inorganic potassium base is $K_2CO_3$; wherein $K_2CO_3$ is present in an amount of about 1 eq. to 10 eq. (notably about 1.5 eq. to 5 eq.; especially about 2 eq. to 2.5 eq.) with respect to the compound of Formula (II).

5) Another embodiment relates to the process according to any one of embodiments 1) to 4), wherein 1H-1,2,3-triazole is present in an amount of about 1 eq. to 10 eq. (notably about 1.5 eq. to 5 eq.; especially about 2 eq.) with respect to the compound of Formula (II).

6) Another embodiment relates to the process according to any one of embodiments 1) to 5), wherein said process is conducted in the presence of a ligand selected from 8-hydroxyquinoline, N1,N2-dimethylcyclohexan-1,2-diamine, and N,N-dimethyl-ethylene-diamine; wherein said ligand is present in an amount of about 0.01 eq. to 0.5 eq. (notably about 0.05 eq. to 0.2 eq.; especially about 0.1 eq.) with respect to the compound of Formula (II).

7) Another embodiment relates to the process according to any one of embodiments 1) to 5), wherein said process is conducted in the absence of a ligand.

8) Another embodiment relates to the process according to any one of embodiments 1) to 7), wherein said process is conducted in presence of
  a solvent which is a water miscible ether solvent (especially dioxane); wherein said water miscible ether solvent is present in an amount of about 5 to 100 vol (notably about 10 to 50 vol, especially about 20 to 40 vol) with respect to the compound of Formula (II); and water, especially in an amount of about 0.05 to 2 vol (notably about 0.1 to 1 vol) with respect to the compound of Formula (II);

wherein preferably the ratio of water miscible ether solvent to water greater than about 10:1 (v/v); notably about 10:1 to 200:1 (v/v); especially about 20:1 to 100:1 (v/v); in particular about 30:1 to 80:1 (v/v).

9) Another embodiment relates to the process according to embodiment 8), wherein, prior to the isolation of the crystalline compound of Formula ($I_K$) from the reaction mixture by solid-liquid separation, the amount of water in the reaction mixture is reduced; wherein especially the total volume of the reaction mixture is reduced to a volume of about 50% to 80% (especially of about 80% to 90%) of the original volume (e.g. by evaporation under reduced pressure, or by distillation at atmospheric pressure).

10) Another embodiment relates to the process according to embodiment 9), wherein, prior to the isolation of the crystalline compound of Formula ($I_K$) from the reaction mixture by solid-liquid separation, and subsequently to the step of embodiment 9), further water miscible ether solvent is added to the reaction mixture (wherein especially the evaporated volume of the reaction mixture is replaced by about the same volume of said water miscible ether solvent).

11) Another embodiment relates to the process according to any one of embodiments 1) to 10), wherein, prior to the isolation of the crystalline compound of Formula ($I_K$) from the reaction mixture by solid-liquid separation, said reaction mixture is cooled to a temperature of below about 50° C., especially to about 20° C. to 40° C.

12) Another embodiment relates to the process according to embodiment 11), wherein said cooling of the reaction mixture is achieved within about 2 hours or less, especially within about 1 hour or less.

Whereas not encompassed in the scope of the process of embodiment 1), the process of embodiments 1) to 12) is, in analogy and by using an inorganic sodium base (in particular $Na_2CO_3$) replacing the inorganic potassium base, also applicable for the preparation of crystalline and regioisomerically essentially pure 5-methyl-2-(2H-[1,2,3]triazol-2-yl)-benzoic acid sodium salt.

13) A second aspect of the invention relates to crystalline forms of the compound of Formula ($I_K$):

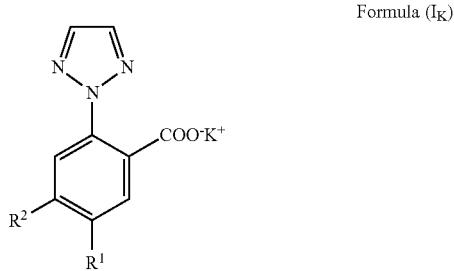

Formula ($I_K$)

wherein $R^1$ represents methoxy and $R^2$ represents hydrogen (i.e. such compound of Formula ($I_K$) is crystalline 5-methoxy-2-(2H-[1,2,3]triazol-2-yl)-benzoic acid potassium salt); characterized by:
a) the presence of peaks in the X-ray powder diffraction diagram at the following angles of refraction 2θ: 6.7°, 7.4°, 15.4°, 23.3°, 27.0°; or
b) the presence of peaks in the X-ray powder diffraction diagram at the following angles of refraction 2θ: 10.8°, 15.1°, 25.0°, 25.9°, 27.1° or wherein $R^1$ represents hydrogen and $R^2$ represents methyl (i.e. such compound of Formula ($I_K$) is crystalline 4-methyl-2-(2H-[1,2,3]triazol-2-yl)-benzoic acid potassium salt); characterized by:
the presence of peaks in the X-ray powder diffraction diagram at the following angles of refraction 2θ: 5.4°, 10.7°, 16.1°, 21.6°, 27.0°.

It is understood, that the crystalline forms according to embodiment 13) comprise the crystalline potassium salts of the respective 2-(2H-[1,2,3]triazol-2-yl)-benzoic acid derivative, i.e. the respective crystalline compound of Formula ($I_K$). Furthermore, said crystalline forms may comprise non-coordinated and/or coordinated solvent. Coordinated solvent is used herein as term for a crystalline solvate. Likewise, non-coordinated solvent is used herein as term for physiosorbed or physically entrapped solvent (definitions according to Polymorphism in the Pharmaceutical Industry (Ed. R. Hilfiker, VCH, 2006), Chapter 8: U. J. Griesser: The Importance of Solvates). The crystalline forms according to embodiment 13) in particular comprise no coordinated water, but may comprise non-coordinated water.

14) Another embodiment relates to crystalline 5-methoxy-2-(2H-[1,2,3]triazol-2-yl)-benzoic acid potassium salt according to embodiment 13); characterized by:
a. the presence of peaks in the X-ray powder diffraction diagram at the following angles of refraction 2θ: 6.7°, 7.4°, 8.7°, 15.4°, 16.4°, 20.2°, 23.3°, 24.4°, 27.0°, 28.1°; or
b. the presence of peaks in the X-ray powder diffraction diagram at the following angles of refraction 2θ: 8.4°, 10.8°, 12.3°, 15.1°, 17.5°, 25.0°, 25.9°, 27.1°, 27.9°, 28.8°.

15) Another embodiment relates to crystalline 5-methoxy-2-(2H-[1,2,3]triazol-2-yl)-benzoic acid potassium salt according to embodiment 13); characterized by the presence of peaks in the X-ray powder diffraction diagram at the following angles of refraction 2θ: 10.8°, 15.1°, 25.0°, 25.9°, 27.1° (in particular at 8.4°, 10.8°, 12.3°, 15.1°, 17.5°, 25.0°, 25.9°, 27.1°, 27.9°, 28.8°); which has a melting point of about 280° C., wherein melting is concomitant with exothermic degradation as determined by differential scanning calorimetry (e.g. by using the method as described herein).

16) Another embodiment relates to crystalline 4-methyl-2-(2H-[1,2,3]triazol-2-yl)-benzoic acid potassium salt according to embodiment 13); characterized by the presence of peaks in the X-ray powder diffraction diagram at the following angles of refraction 2θ: 5.4°, 8.8°, 10.7°, 12.0°, 16.1°, 21.6°, 23.3°, 24.2°, 27.0°, 32.6°.

17) Another embodiment relates to crystalline 4-methyl-2-(2H-[1,2,3]triazol-2-yl)-benzoic acid potassium salt according to embodiment 16); characterized by the presence of peaks in the X-ray powder diffraction diagram at the following angles of refraction 2θ: 5.4°, 10.7°, 16.1°, 21.6°, 27.0° (in particular at 5.4°, 8.8°, 10.7°, 12.0°, 16.1°, 21.6°, 23.3°, 24.2°, 27.0°, 32.6°); which has a melting point of about 277° C., wherein melting is concomitant with exothermic degradation as determined by differential scanning calorimetry (e.g. by using the method as described herein).

Further disclosed is a crystalline form of 5-methyl-2-(2H-[1,2,3]triazol-2-yl)-benzoic acid sodium salt; characterized by the presence of peaks in the X-ray powder diffraction diagram at the following angles of refraction 2θ: 6.5°, 7.7°, 11.9°, 15.3°, 17.5°, 19.0°, 20.1°, 21.7°, 23.6°, 25.6°.

18) A third aspect of the invention relates to a process according to any one of embodiments 1) to 12), wherein said isolated crystalline compound of Formula ($I_K$):

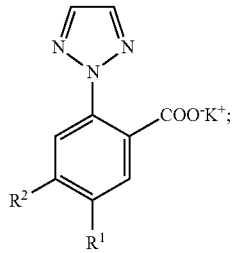

Formula ($I_K$)

wherein
R$^1$ represents methoxy and R$^2$ represents hydrogen; or
R$^1$ represents hydrogen and R$^2$ represents methyl;
is further transformed into the respective crystalline 2-(2H-[1,2,3]triazol-2-yl)-benzoic acid derivative, a compound of Formula (I):

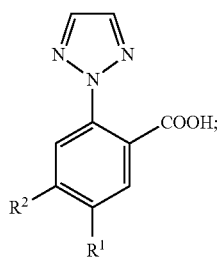

Formula (I)

[wherein it is understood that for the compound of Formula (I), R$^1$ and R$^2$ are as defined before for the compound of Formula ($I_K$)]
said process comprising a crystallization step from acidic aqueous medium.

19) Another embodiment relates to the process according to embodiment 18), wherein said process comprises the steps:
(i) preparing a basic aqueous solution comprising the compound of Formula (I); especially by dissolving said isolated crystalline compound of Formula ($I_K$) in an aqueous medium [wherein it is understood that such aqueous medium may be water, or a basic aqueous medium (such as an aqueous solution of an alkali metal hydroxide, carbonate or hydrogen carbonate];
(ii) crystallizing said compound of Formula (I) by acidifying a basic aqueous solution comprising said compound of Formula (I); and
(iii) isolating said crystalline compound of Formula (I) by solid-liquid separation.

Said process of embodiments 18) and 19) thus involves a salt break in aqueous medium, and comprises the crystallization of the compounds of Formula (I) in regioisomerically essentially pure form (especially in a regioisomeric ratio of greater than 98:2, in particular in regioisomerically pure form).

20) Another embodiment, thus, relates to the process according to embodiments 18) or 19), wherein the regioisomeric ratio of the isolated crystalline compound of formula (I); i.e. the ratio of [compound of Formula (I)]: [compound of Formula ($I_R$)]:

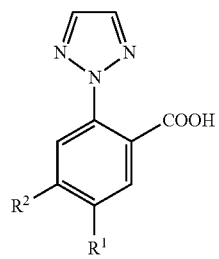

Formula (I)

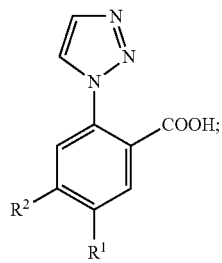

Formula ($I_R$)

is at least about 98:2; wherein especially the crystalline compound of Formula (I) is obtained in regioisomerically pure form.

21) Another embodiment relates to the process according to any one of embodiments 18) to 20), wherein said crystallization step [corresponding to step (ii) of embodiment 19)] is performed at a temperature of about 30° C. to 60° C.; preferably at a temperature of about 40° C. to 55° C.; especially at about 40° C. to 50° C.

22) Another embodiment relates to the process according to any one of embodiments 18) to 21), wherein said crystalline compound of Formula (I) is isolated by solid-liquid separation [corresponding to step (iii) of embodiment 19)]; wherein said solid-liquid separation is performed at a temperature of about 10° C. to 50° C.; preferably at a temperature of about 20° C. to 45° C., especially about 30° C. to 40° C.

23) Another embodiment relates to the process according to any one of embodiments 18) to 22), wherein, prior to the crystallization step [corresponding to step (ii) of embodiment 19)], an aqueous solution of said compound of Formula (I) [e.g. obtained by dissolving said compound of Formula ($I_K$) in aqueous medium according to step (i) of embodiment 19)] is subjected to:
a) a filtration step (e.g. using standard filtration techniques; or standard filtration techniques and, in addition, a filtration through active charcoal); and/or
b) a washing step comprising a sequence of at least two liquid-liquid separations wherein the compound of Formula (I) is first extracted into an organic non water-miscible solvent; and, subsequently, extracted from said organic non water-miscible solvent into a basic aqueous solution; wherein, subsequently, said basic aqueous solution is used for the crystallization step [corresponding to step (ii) of embodiment 19)] of the process according to any one of embodiments 18) to 21).

Such washing step comprising a sequence of liquid-liquid separations according to variant b) of embodiment 23) refers for example to the following steps:
(b1) acidification of a basic aqueous solution comprising the compound of Formula (I), for example obtained according to step (i) of embodiment 19); and extraction of the compound of Formula (I) into an organic non water-miscible solvent (such as especially tert.-butyl-methyl ether (TBME));

(b2) optional washing of the organic phase obtained in step (b1) with an acidic aqueous solution (such as an aqueous inorganic acid solution, especially an aqueous sulfuric acid or hydrochloric acid solution); and (b3) extraction of the compound of Formula (I) from the organic phase obtained in step (b1) or (b2) into a basic aqueous medium (such as an alkali metal hydroxide or carbonate solution, especially an aqueous sodium hydroxide or potassium hydroxide solution); wherein, subsequently, said basic aqueous solution is used for the crystallization step [corresponding to step (ii) of embodiment 19)] according to any one of embodiments 18) to 21).

24) Another embodiment relates to the process according to any one of embodiments 18) to 23), wherein, in the crystallization step [corresponding to step (ii) of embodiment 19)], an aqueous inorganic acid solution is used to acidify said basic aqueous solution [wherein such aqueous inorganic acid solution is notably aqueous sulfuric acid (especially about 10% to 30% aqueous sulfuric acid; in particular about 20% aqueous sulfuric acid); or aqueous hydrochloric acid (especially about 10% to 32% aqueous hydrochloric acid; in particular about 32% aqueous hydrochloric acid)].

25) Another embodiment relates to the process according to any one of embodiments 18) to 24), wherein, in the crystallization step [corresponding to step (ii) of embodiment 19)], said acidic aqueous solution has a pH of below about 4, especially below about 3, in particular between about 1 to 3.

26) Another embodiment relates to the process according to any one of embodiments 18) to 25), wherein, during the crystallization step [corresponding to step (ii) of embodiment 19)], seeding crystals are added to the aqueous mixture; wherein at the time when said seeding crystals are added, the pH of said mixture is about 6 or below, especially about 4 to 3.

Whereas not encompassed in the scope of the process of embodiment 18), the process of embodiments 18) to 26) is, in analogy and by starting from crystalline and regioisomerically essentially pure 5-methyl-2-(2H-[1,2,3]triazol-2-yl)-benzoic acid sodium salt rather than from a compound of Formula ($I_K$), also applicable for the preparation of crystalline and regioisomerically essentially pure 5-methyl-2-(2H-[1,2,3]triazol-2-yl)-benzoic acid.

27) A fourth aspect of the invention relates to crystalline forms of the compound of Formula (I):

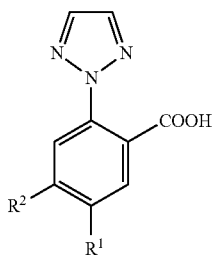

Formula (I)

wherein $R^1$ represents methoxy and R represents hydrogen (i.e. such compound of Formula (I) is crystalline 5-methoxy-2-(2H-[1,2,3]triazol-2-yl)-benzoic acid);

a) characterized by the presence of peaks in the X-ray powder diffraction diagram at the following angles of refraction 2θ: 5.7°, 11.5°, 17.2°, 21.3°, 25.0°; or b) characterized by the presence of peaks in the X-ray powder diffraction diagram at the following angles of refraction 2θ: 11.4°, 12.3°, 15.5°, 21.3°, 23.6°;

or wherein $R^1$ represents hydrogen and $R^2$ represents methyl (i.e. such compound of Formula (I) is crystalline 4-methyl-2-(2H-[1,2,3]triazol-2-yl)-benzoic acid); characterized by the presence of peaks in the X-ray powder diffraction diagram at the following angles of refraction 2θ: 6.2°, 12.5°, 15.1°, 18.8°, 25.2°.

It is understood, that the crystalline forms according to embodiment 27) comprise the respective crystalline 2-(2H-[1,2,3]triazol-2-yl)-benzoic acid derivative, i.e. the respective crystalline compound of Formula (I). Furthermore, said crystalline forms may comprise non-coordinated and/or coordinated solvent. Coordinated solvent is used herein as term for a crystalline solvate. Likewise, non-coordinated solvent is used herein as term for physiosorbed or physically entrapped solvent (definitions according to Polymorphism in the Pharmaceutical Industry (Ed. R. Hilfiker, VCH, 2006), Chapter 8: U. J. Griesser: The Importance of Solvates). The crystalline forms according to embodiment 27) in particular comprise no coordinated water, but may comprise for example non-coordinated water.

28) Another embodiment relates to crystalline 5-methoxy-2-(2H-[1,2,3]triazol-2-yl)-benzoic acid according to embodiment 27); characterized by the presence of peaks in the X-ray powder diffraction diagram at the following angles of refraction 2θ: 5.7°, 11.5°, 16.0°, 17.2°, 18.9°, 19.7°, 21.3°, 23.7°, 25.0°, 27.9°.

29) Another embodiment relates to crystalline 5-methoxy-2-(2H-[1,2,3]triazol-2-yl)-benzoic acid according to embodiment 27); characterized by the presence of peaks in the X-ray powder diffraction diagram at the following angles of refraction 2θ: 5.7°, 11.5°, 17.2°, 21.3°, 25.0° (in particular at 5.7°, 11.5°, 16.0°, 17.2°, 18.9°, 19.7°, 21.3°, 23.7°, 25.0°, 27.9°); which has a melting point of about 80° C. as determined by differential scanning calorimetry (e.g. by using the method as described herein).

30) Another embodiment relates to crystalline 5-methoxy-2-(2H-[1,2,3]triazol-2-yl)-benzoic acid according to embodiment 27); characterized by the presence of peaks in the X-ray powder diffraction diagram at the following angles of refraction 2θ: 11.4°, 12.3°, 14.6°, 15.5°, 21.3°, 23.1°, 23.6°, 24.8°, 25.6°, 29.9°.

31) Another embodiment relates to crystalline 5-methoxy-2-(2H-[1,2,3]triazol-2-yl)-benzoic acid according to embodiment 27); characterized by the presence of peaks in the X-ray powder diffraction diagram at the following angles of refraction 2θ: 5.7°, 11.5°, 17.2°, 21.3°, 25.0° (in particular at 11.4°, 12.3°, 14.6°, 15.5°, 21.3°, 23.1°, 23.6°, 24.8°, 25.6°, 29.9°); which has a melting point of about 130-131° C. as determined by differential scanning calorimetry (e.g. by using the method as described herein).

32) Another embodiment relates to crystalline 4-methyl-2-(2H-[1,2,3]triazol-2-yl)-benzoic acid according to embodiment 27); characterized by the presence of peaks in the X-ray powder diffraction diagram at the following angles of refraction 2θ: 6.2°, 11.3°, 12.5°, 13.3°, 15.1°, 17.0°, 17.8°, 18.8°, 22.6°, 25.2°.

33) Another embodiment relates to crystalline 4-methyl-2-(2H-[1,2,3]triazol-2-yl)-benzoic acid according to embodiment 27); characterized by the presence of peaks in the X-ray powder diffraction diagram at the following angles of refraction 2θ: 6.2°, 12.5°, 15.1°, 18.8°, 25.2° (in particular at 6.2°, 11.3°, 12.5°, 13.3°, 15.1°, 17.0°, 17.8°, 18.8°, 22.6°, 25.2°); which has a melting point of about 125° C. as determined by differential scanning calorimetry (e.g. by using the method as described herein).

Further disclosed is a crystalline form of 5-methyl-2-(2H-[1,2,3]triazol-2-yl)-benzoic acid; characterized by the presence of peaks in the X-ray powder diffraction diagram at the following angles of refraction 2θ: 11.8°, 13.0°, 13.9°, 16.6°, 21.1°, 21.9°, 23.3°, 23.8°, 26.6°, 28.0°. Said crystalline form has a melting point of about 173° C. as determined by differential scanning calorimetry (e.g. by using the method as described herein).

34) A further aspect of the present invention relates to a process according to any one of embodiments 18) to 26), wherein the crystalline compound of Formula (I) which in this particular case is crystalline 5-methoxy-2-(2H-[1,2,3] triazol-2-yl)-benzoic acid; especially crystalline 5-methoxy-2-(2H-[1,2,3]triazol-2-yl)-benzoic acid according to embodiments 28) or 29); is further transformed to the compound (S)-(2-(5-chloro-4-methyl-1H-benzo[d]imidazol-2-yl)-2-methylpyrrolidin-1-yl)(5-methoxy-2-(2H-1,2,3-triazol-2-yl)phenyl)methanone; or a pharmaceutically acceptable salt thereof. Likewise, the present invention relates to the use of crystalline 5-methoxy-2-(2H-[1,2,3] triazol-2-yl)-benzoic acid; especially of crystalline 5-methoxy-2-(2H-[1,2,3]triazol-2-yl)-benzoic acid according to embodiments 28) or 29); in the preparation of (S)-(2-(5-chloro-4-methyl-1H-benzo[d]imidazol-2-yl)-2-methylpyrrolidin-1-yl)(5-methoxy-2-(2H-1,2,3-triazol-2-yl) phenyl)methanone; or of a pharmaceutically acceptable salt thereof.

Such transformation according to embodiment 34) is described especially in WO2013/182972, WO2015/083071, WO2015/083070 and WO2015/083094, which references are incorporated in its entirety: In particular said crystalline 5-methoxy-2-(2H-[1,2,3]triazol-2-yl)-benzoic acid is coupled (e.g. under standard amide coupling conditions) with (S)-5-chloro-4-methyl-2-(2-methylpyrrolidin-2-yl)-1H-benzo[d]imidazole to yield (S)-(2-(5-chloro-4-methyl-1H-benzo[d]imidazol-2-yl)-2-methylpyrrolidin-1-yl)(5-methoxy-2-(2H-1,2,3-triazol-2-yl)phenyl)methanone, which is an orexin receptor antagonist.

Alternatively such multistep transformation may comprise the step of coupling 5-methoxy-2-(2H-1,2,3-triazol-2-yl) benzoic acid with methyl (S)-2-methylpyrrolidine-2-carboxylate hydrochloride under standard amide coupling conditions to yield methyl (S)-1-(5-methoxy-2-(2H-1,2,3-triazol-2-yl) benzoyl)-2-methylpyrrolidine-2-carboxylate, which is further transformed to (S)-(2-(5-chloro-4-methyl-1H-benzo[d]imidazol-2-yl)-2-methylpyrrolidin-1-yl) (5-methoxy-2-(2H-1,2,3-triazol-2-yl)phenyl)methanone or its hydrochloride in analogy to the methods disclosed in the experimental part (wherein said further transformation comprises a sequence of hydrolysis, coupling of carboxylic acid with 4-chloro-3-methylbenzene-1,2-diamine hydrochloride and a cyclization).

For avoidance of doubt, substituents of the benzimidazole moiety may be attached in the position(s) ortho to the bridgehead atoms (i.e. attached in position(s) 4 and/or 7), and/or in the position(s) meta to the bridgehead atoms, (i.e. attached in position(s) 5 and/or 6). It is understood that the two ortho, and, respectively, the two meta positions are considered equivalent. For example, the group 5-chloro-4-methyl-1H-benzoimidazol-2-yl is understood to signify the same group as 6-chloro-7-methyl-3H-benzoimidazol-2-yl, and encompasses its tautomeric form 5-chloro-4-methyl-3H-benzoimidazol-2-yl/6-chloro-7-methyl-1H-benzoimidazol-2-yl.

35) A further aspect of the present invention relates to a process according to any one of embodiments 18) to 26), wherein the crystalline compound of Formula (I) which in this particular case is crystalline 4-methyl-2-(2H-[1,2,3] triazol-2-yl)-benzoic acid; especially crystalline 4-methyl-2-(2H-[1,2,3]triazol-2-yl)-benzoic acid according to embodiments 32) or 33); is further transformed to the compound (4-methyl-2-[1,2,3]triazol-2-yl-phenyl)-[(R)-3-(3-[1,2,3]triazol-2-yl-benzyl)-morpholin-4-yl]-methanone.

Such multistep transformation according to embodiment 35) is described especially in WO2013/068935, which reference is incorporated in its entirety:

In particular said crystalline 4-methyl-2-(2H-[1,2,3]triazol-2-yl)-benzoic acid is coupled (e.g. under standard amide coupling conditions) with (R)-3-(3-(2H-[1,2,3]triazol-2-yl)benzyl)morpholine (intermediate A15 of WO2013/068935) to yield (4-methyl-2-[1,2,3]triazol-2-yl-phenyl)-[(R)-3-(3-[1,2,3]triazol-2-yl-benzyl)-morpholin-4-yl]-methanone, which is an orexin receptor antagonist.

Where the plural form is used for compounds, salts, pharmaceutical compositions, diseases and the like, this is intended to mean also a single compound, salt, or the like.

For avoidance of any doubt, whenever one of the above embodiments refers to "peaks in the X-ray powder diffraction diagram at the following angles of refraction 2θ", said X-ray powder diffraction diagram is obtained by using combined Cu Kα1 and Kα2 radiation, without Kα2 stripping; and it should be understood that the accuracy of the 2θ values as provided herein is in the range of +/−0.1-0.2°. Notably, when specifying an angle of refraction 2theta (2θ) for a peak in the invention embodiments and the claims, the 2θ value given is to be understood as an interval from said value minus 0.2° to said value plus 0.2° (2θ+/−0.2°); and preferably from said value minus 0.10 to said value plus 0.1 (2θ+/−0.1).

Definitions provided herein are intended to apply uniformly to the compounds of formula (I) and ($I_K$), and to the processes as defined in any one of embodiments 1) to 35), and, mutatis mutandis, throughout the description and the claims unless an otherwise expressly set out definition provides a broader or narrower definition. It is well understood that a definition or preferred definition of a term defines and may replace the respective term independently of (and in combination with) any definition or preferred definition of any or all other terms as defined herein.

The term "solid-liquid separation" refers to routine solid-liquid separation techniques well known to a skilled person (see for example Perry's Chemical Engineers' Handbook, 7$^{th}$ edition, Perry, R. H.; Green, D. W. McGraw-Hill 1997). In particular, the term includes techniques such as filtration, centrifugation, and gravity sedimentation; especially filtration.

The term "liquid-liquid extraction" refers to routine liquid-liquid extraction or washing techniques well known to a skilled person (see for example Perry's Chemical Engineers' Handbook, 7$^{th}$ edition, Perry, R. H.; Green, D. W. McGraw-Hill 1997). In particular the term includes washing or extraction techniques using settlers, cyclones, centrifuges, mixer-settler, all kinds of continuous contact equipment; distillation: batch and continuous distillation; and supercritical fluid separation techniques.

Unless used regarding temperatures, the term "about" placed before a numerical value "X" refers in the current application to an interval extending from X minus 10% of X to X plus 10% of X, and preferably to an interval extending from X minus 5% of X to X plus 5% of X (wherein it is well understood that values below 0%, respectively higher than 100%, are not applicable). In case the term about is placed before a range, the respective interval is to be applied to both values of the range. In the particular case of temperatures, the term "about" placed before a temperature "Y" refers in the current application to an interval extending from the temperature Y minus 10° C. to Y plus 10° C.; and preferably, in case the temperature is at least 30° C. to an interval extending from Y minus 5° C. to Y plus 5° C.; or, in case the temperature is below 30° C., to an interval extending from Y minus 2° C. to Y plus 2° C.

Whenever the word "between" or "to" is used to describe a numerical range, it is to be understood that the end points of the indicated range are explicitly included in the range. For example: if a temperature range is described to be between 40° C. and 80° C. (or 40° C. to 80° C.), this means that the end points 40° C. and 80° C. are included in the range; or if a variable is defined as being an integer between 1 and 4 (or 1 to 4), this means that the variable is the integer 1, 2, 3, or 4.

The expression % w/w refers to a percentage by weight compared to the total weight of the composition considered. If not explicitly indicated a % value is to be understood as % w/w. The expression (wt/wt) relating to a ratio refers to a ratio by weight of the two components considered. Likewise, the expression v/v refers to a ratio by volume of the two components considered. Likewise, the expression % a/a refers to the purity with respect to area under the curve (i.e. integral) in a chromatogram, preferably measuring the UV absorption. The expression "vol" signifies volumes (in L, e.g. of solvent) per weight (in kg, e.g. of reactant). For example 10 vol signifies 10 liters (of solvent) per kg (of reactant).

The term "enriched", for example when used in the context of regioisomers/enantiomers or diastereoisomers is understood in the context of the present invention to mean especially that the respective regioisomer/enantiomer/diastereoisomer is present in a ratio (mutatis mutandis:purity) as explicitly specified; usually in a ratio of at least 70:30, notably of at least 80:20, and especially of at least 90:10 (mutatis mutandis: purity of 70%/80%/90%) with respect to the respective other regioisomer/enantiomer/diastereoisomer. Preferably the term refers to the respective essentially pure regioisomer/enantiomer/diastereoisomer.

The term "essentially", for example when used in a term such as "essentially pure" is understood in the context of the present invention to mean especially that the respective stereoisomer/composition/compound etc. consists in an amount of at least 90, notably of at least 95, and especially of at least 98 percent by weight of the respective pure regioisomer/stereoisomer/composition/compound etc. The term "pure when used in the context of a certain regioisomer/enantiomer or diastereoisomer is understood in the context of the present invention to mean that the respective other regioisomer(s)/enantiomer(s)/diastereoisomer(s) is/are below 1% (especially it is/they are not detectable) as measured by usual means of analysis such as especially HPLC/LC-MS (in which case it is understood that % refers to a/a % as measured by HPLC/LC-MS).

The term "consisting essentially of" is understood in the context of the present invention to mean especially that the respective composition consists in an amount of at least 90, notably of at least 95, especially of at least 98, and preferably in an amount of 100 percent by weight (i.e. in the meaning of "consisting of") of the respective composition in the amounts as explicitly stated in the respective embodiment.

According to the invention, the compounds of Formulae (I) and ($I_K$) may be manufactured by, or in analogy to, the methods given in embodiments 1) to 12), and 18) to 26) above, or in the experimental part below. The following examples are provided to further illustrate the invention. These examples should not be construed as limiting the invention in any way.

Experimental Part

The commercially available starting materials were used as received without further purification. All temperatures given are internal temperatures and are stated in ° C. Compounds may be characterized by $^1$H-NMR (400 MHz) or $^{13}$C-NMR (100 MHz) (Bruker; chemical shifts are given in ppm relative to the solvent used; multiplicities: s=singlet, d=doublet, t=triplet, p=pentuplet, hex=hexet, hept=heptet, m=multiplet, br=broad, coupling constants are given in Hz); internal standard for quantitative NMR was 1,4-dimethoxybenzene; or by LC-MS, $t_R$ is given in minutes.

| LC-MS method 1 Waters iClass, Thermo MSQ Plus and DAD | |
|---|---|
| Injection volume: | 0.15 μL |
| Column: | Zorbax RRHD SB-AQ, 1.81 μm, 2.1 × 50 mm |
| Column flow: | 0.8 mL/min |
| Eluent: | Eluent A: Water, 0.04% TFA |
| | Eluent B: Acetonitrile |
| Gradient: | 0.00 min 5% B |
| | 1.20 min 95% B |
| | 1.90 min 95% B |
| | 2.1 min 5% B |
| Temperature: | 40° C. |

| LC-MS method 2: Aqilent G1956B, G1312B and DAD | |
|---|---|
| Injection volume: | 2 μL |
| Column: | Kinetex C18, 2.6 micron, 2.1 × 50 mm |
| Column flow: | 1 mL/min |
| Eluent: | Eluent A: Water, 0.08% TFA |
| | Eluent B: Acetonitrile, 0.012% TFA |
| Gradient: | 0.00 min 5% B |
| | 2.0 min 95% B |
| | 2.8 min 95% B |
| | 3.0 min 5% B |
| Temperature: | 40° C. |

X-Ray Powder Diffraction Analysis

X-ray powder diffraction patterns were collected on a Bruker D8 Advance X-ray diffractometer equipped with a Lynxeye detector operated with CuK$_\alpha$-radiation in reflection mode (coupled two Theta/Theta). Typically, the X-ray tube was run at of 4 kV/40 mA. A step size of 0.020 (2θ) and a step time of 76.8 sec over a scanning range of 3-500 in 2θ were applied. The divergence slit was set to fixed 0.3. Powders were slightly pressed into a silicon single crystal sample holder with depth of 0.5 mm and samples were rotated in their own plane during the measurement. Diffraction data are reported using combined Cu Kα1 and Kα2 radiation, without Kα2 stripping. The accuracy of the 2θ values as provided herein is in the range of +/−0.1-0.2° as it is generally the case for conventionally recorded X-ray powder diffraction patterns.

Differential Scanning Calorimetry

DSC data were collected on a Mettler Toledo STARe System (DSC822e module, measuring cell with ceramic sensor and STAR software version 13) equipped with a 34 position auto-sampler. The instrument was calibrated for energy and temperature using certified indium. A nitrogen purge of 20 mL/min was maintained over the sample during measurement.

For the salts, typically 1-5 mg of sample was weighed into a Mettler Toledo 40 micoliter aluminum pan, that was automatically pierced and placed into the furnace. A heating rate of 4° C./min was applied in the range from 20° C. to 500° C.

For the acids, typically 1-5 mg of sample was weighed into a Tüv Süd (Switzerland) M20 high pressure pan, that was hermetically sealed and placed manually into the furnace. A heating rate of 4° C./min was applied in the range from 20° C. to 400° C.

Melting points are reported as peak temperatures.

Abbreviations (as Used Herein or in the Description Above)

aq. aqueous
atm Atmosphere
eq. equivalent(s)
DMF N,N-Dimethylformamide
DMSO Dimethyl sulfoxide
EtOAc Ethyl acetate
Ex. Example
Fig Figure
GC-MS gas chromatography-mass spectrometry
h hour(s)
HPLC High performance liquid chromatography
IPC in-process control
iPrMgCl isopropyl magnesium chloride
LC-MS liquid chromatography-mass spectrometry
M Exact mass (as used for LC-MS)
min minute(s)
MHz Megahertz
min Minute(s)
MP Melting Point
MS Mass spectroscopy
N Normality
NMR nuclear magnetic resonance
$^1$H-NMR Nuclear magnetic resonance of the proton
org. organic
RT Room temperature
TBME tert.-butyl methyl ether
TFA trifluoroacetic acid
THF Tetrahydrofuran
$t_R$ retention time
sat. saturated
soln. solution
UV Ultra violet
% a/a area % (purity by area %)

EXAMPLES

Reference Example 1

Synthesis of 5-methoxy-2-(2H-1,2,3-triazol-2-yl)benzoic acid 4,5-dibromo-2-(4-methoxy-2-nitrophenyl)-2H-1,2,3-triazole 4-Fluoro-3-nitroanisole (3.44 g, 1 eq.), 4,5-dibromo-2H-1,2,3-triazole (4.56 g, 1 eq.)[1], $K_2CO_3$ (2.78 g, 1 eq.) and DMF (30 mL) are heated to 110° C. for 32 h. The reaction mixture is cooled to 22° C. and treated with water (70 mL). The resulting suspension is filtered, washed with water (15 mL). The product is slurried in isopropanol (40 mL), filtered and dried under reduced pressure to yield a white solid. Yield: 6.42 g, 84%. Purity: 100% a/a (LC-MS method 2). $^1$H NMR (400 MHz, CDCl$_3$) δ: 7.71 (d, J=8.9 Hz, 1H), 7.47 (d, J=2.8 Hz, 1H), 7.25 (dd, J$_1$=2.8 Hz, J$_2$=8.9 Hz, 1H), 3.97 (s, 3H).

[1] X. Wang, L. Zhang, D. Krishnamurthy, C. H. Senanayake, P. Wipf Organic Letters 2010 12 (20), 4632-4635.

5-methoxy-2-(2H-1,2,3-triazol-2-yl)aniline 4,5-Dibromo-2-(4-methoxy-2-nitrophenyl)-2H-1,2,3-triazole (2 g, 1 eq.), sodium acetate (1.3 g, 3 eq.), and 10% Pd/C 50% water wet (0.3 g) is suspended in EtOAc (10 mL). The mixture is heated to 50° C. and set under hydrogen until conversion is complete. The reaction mixture is filtered over Celite. The filtrate is washed with 1 N NaOH (10 mL) and water (15 mL). The organic layer is concentrated under reduced pressure to yield an oil. Yield: 0.95 g, 94%. Purity: 96% a/a (LC-MS method 2). $^1$H NMR (400 MHz, DMSO) δ: 8.05 (s, 2H), 7.53 (d, J=8.9 Hz, 1H), 6.49 (d, J=2.7 Hz, 1H), 6.30 (dd, J$_1$=2.7 Hz, J$_2$=8.9 Hz, 1H), 5.94 (s, 2H), 3.74 (s, 3H).

5-methoxy-2-(2H-1,2,3-triazol-2-yl)aniline monosulfate

5-Methoxy-2-(2H-1,2,3-triazol-2-yl)aniline (455 g, 1 eq) is dissolved in isopropanol (3 L). To the solution is added conc. $H_2SO_4$ (235 g, 1 eq.) below 40° C. The suspension is cooled to 20° C. and filtered. The cake is washed with isopropanol (700 mL) and TBME (1.5 L). The product is dried to obtain a white solid. Yield: 627 g, 91%. Purity: 100% a/a (LC-MS method 2).

2-(2-iodo-4-methoxyphenyl)-2H-1,2,3-triazole

5-Methoxy-2-(2H-1,2,3-triazol-2-yl)aniline monosulfate (200 g, 1 eq.) is dissolved in 2 M aq. $H_2SO_4$ soln. (1.4 L) and cooled to −5° C. To the solution is added a solution of sodium nitrite (62 g, 1.3 eq.) in water (600 mL) at −5 to 0° C. The mixture is stirred at 0° C. for 30 min and then added to a preheated mixture of KI (161 g, 1.4 eq.) in water (700 mL) at 65° C. The resulting solution is stirred at 60° C. for 20 min, cooled to 20° C. and treated with a soln. of sulfamic acid (27 g, 0.4 eq.) in water (120 mL). The mixture is extracted with isopropyl acetate (2 L). The organic layer is washed with a mixture of 2 N NaOH (500 mL) and 40% NaHSO$_3$ soln. (100 mL), and a mixture of 1 N HCl (50 mL) and water (500 mL). The organic layer is concentrated to dryness. The residue is dissolved in isopropanol (700 mL) and cooled to 0° C. The resulting suspension is filtered. The solid is dried under reduced pressure. Yield: 164 g, 79%. Purity: 100% a/a (LC-MS method 2). $^1$H NMR (400 MHz, DMSO) δ: 8.08 (s, 2H), 7.57 (d, J=2.8 Hz, 1H), 7.43 (d, J=8.8 Hz, 1H), 7.13 (dd, J$_1$=2.8 Hz, J$_2$=8.8 Hz, 1H), 3.85 (s, 3H).

5-methoxy-2-(2H-1,2,3-triazol-2-yl)benzoic acid 2-(2-Iodo-4-methoxyphenyl)-2H-1,2,3-triazole (200 g, 1 eq.) is dissolved in THF (2 L) and cooled to 0° C. 2 M iPrMgCl soln. in THF (350 mL, 1.05 eq.) is added at 0° C. The mixture is cooled to −20° C. and CO$_2$ (gas) is bubbled into the solution over 30 min until the exothermicity is ceased. To the mixture is added 2 N HCl (600 mL) at 8° C. and concentrated under reduced pressure to remove 2.4 L solvent. The residue is extracted with TBME (1.6 L). The organic layer is washed with 1N HCl (200 mL) and extracted with 1N NaOH (600 mL and 200 mL). The aq. layer is filtered over charcoal (15 g), diluted with water (200 mL) and treated with 32% HCl (160 mL). The resulting suspension is filtered and washed with water (200 mL). Yield: 127 g, 87%. Purity: 100% a/a (LC-MS method 2); MP: 130° C. (DSC goldpan). The obtained product may be re-crystallized from toluene (MP: 130.9° C.) or water (MP: 130° C.).

TABLE

Figure 8:
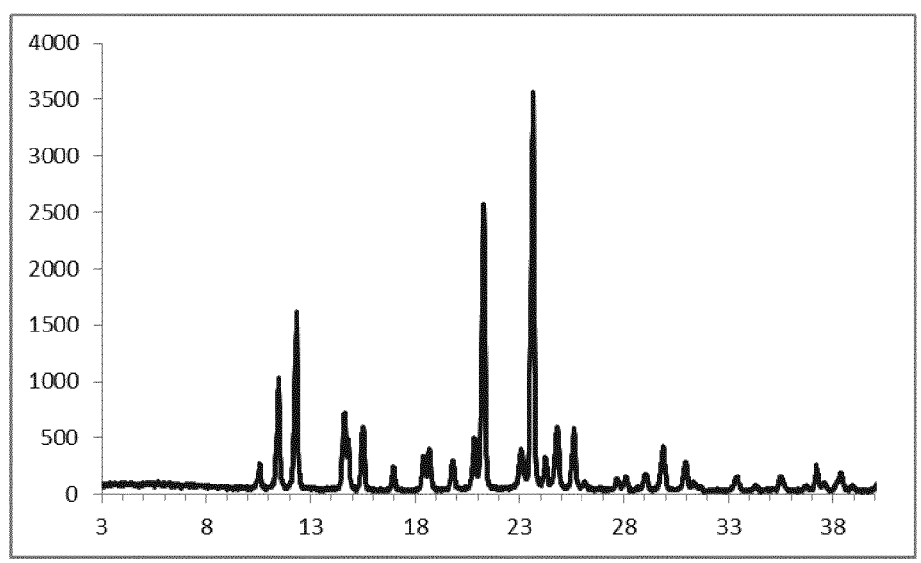
FIG. 8 shows the X-ray powder diffraction diagram of crystalline 5-methoxy-2-(2H-[1,2,3]triazol-2-yl)-benzoic acid as obtained from Reference Example 1. The X-ray diffraction diagram measured with method 2 shows peaks having a relative intensity, as compared to the most intense peak in the diagram, of the following percentages (relative peak intensitites given in parenthesis) at the indicated angles of refraction 2theta (selected peaks from the range 3-40° 2theta are reported): 11.4° (28%), 12.3° (44%), 14.6° (21%), 14.7° (10%), 15.5° (15%), 18.7° (11%), 20.8° (14%), 21.3° (76%), 23.1° (10%), 23.6° (100%), 24.8° (16%), 25.6° (16%), 29.9° (11%).

| Ref 1: Characterisation data for 5-methoxy-2-(2H-1,2,3-triazol-2-yl)benzoic acid in crystalline form 2 (recrystallization from toluene) | | |
|---|---|---|
| Technique | Data Summary | Remarks |
| XRPD | Crystalline | see FIG. 8 |

Reference Example 2

Synthesis of 4-methyl-2-(2H-1,2,3-triazol-2-yl)benzoic acid 4,5-Dibromo-2-(5-methyl-2-nitrophenyl)-2H-1,2,3-triazole 3-Fluoro-4-nitrotoluene (1367 g, 1 eq.), 4,5-dibromo-2H-1,2,3-triazole (1999 g, 1 eq.), $K_2CO_3$ (1340 g, 1.1 eq.) and DMF (11 L) is heated to 75° C. for 15 h. The reaction mixture is cooled to 22° C. and treated with water (18 L). The resulting suspension is filtered, washed with water (4 L). The product is washed with isopropanol (5 L), and dried under reduced pressure to yield a white solid. Yield: 2811 g, 88%. Purity: 100% a/a (LC-MS method 2). $^1$H NMR (400 MHz, DMSO) δ: 8.10 (d, J=8.3 Hz, 1H), 7.86 (d, J=1.0 Hz, 1H), 7.66 (dd, J1=0.9 Hz, J2=8.3 Hz, 1H), 2.51 (s, 3H).

4-Methyl-2-(2H-1,2,3-triazol-2-yl)aniline 4,5-Dibromo-2-(5-methyl-2-nitrophenyl)-2H-1,2,3-triazole (205 g, 1 eq.), sodium acetate (149 g, 3.2 eq.), and 5% Pd/C 50% water wet (37.8 g) is suspended in EtOAc (0.8 L). The mixture is heated to 40-50° C. and set under hydrogen (2 bar) until conversion is complete. The reaction mixture is filtered over Celite. The filtrate is washed with water (300 mL), 2N NaOH (300 mL+250 mL) and water (300 mL). The organic layer is concentrated under reduced pressure to yield a yellow oil. Yield: 132 g, 90%. Purity: 100% a/a (LC-MS method 2). $^1$H NMR (400 MHz, DMSO) δ: 8.09 (s, 2H), 7.48 (d, J=1.3 Hz, 1H), 6.98 (dd, J1=1.8 Hz, J2=8.3 Hz, 1H), 6.85 (d, J=8.2 Hz, 1H), 5.79 (s, 2H), 2.23 (s, 3H).

4-Methyl-2-(2H-1,2,3-triazol-2-yl)aniline monosulfate

4-Methyl-2-(2H-1,2,3-triazol-2-yl) aniline (199 g, 1 eq) is dissolved in isopropanol (1.7 L). To the solution is added conc. $H_2SO_4$ (118 g, 1.05 eq.) below 40° C. The suspension is cooled to 20° C. and filtered. The cake is washed with isopropanol (500 mL). The product is dried to obtain a white solid. Yield: 278 g, 89%. Purity: 100% a/a (LC-MS method 2). $^1$H NMR (400 MHz, DMSO) δ: 8.21 (s, 2H), 7.70 (s, 1H), 7.23 (s, 2H), 2.35 (s, 3H).

2-(2-iodo-5-methylphenyl)-2H-1,2,3-triazole

4-Methyl-2-(2H-1,2,3-triazol-2-yl)aniline monosulfate (1553 g, 1 eq.) is dissolved in 1 M aq. $H_2SO_4$ soln. (11 L) and cooled to −5° C. To the solution is added a solution of sodium nitrite (433 g, 1.1 eq.) in water (4 L) at −5 to 0° C. The mixture is stirred at 0° C. for 30 min and then added to a preheated mixture of potassium iodide (1325 g, 1.4 eq.) in water (4 L) at 55-70° C. The resulting solution is stirred at 60° C. for 20 min, cooled to 20° C. and treated with a soln. of sulfamic acid (220 g, 0.4 eq.) in water (900 mL). The mixture is extracted with isopropyl acetate (13 L). The organic layer is washed with a mixture of 2 N NaOH (3.5 L) and 40% $NaHSO_3$ soln. (330 g), and a mixture of 1 N HCl (280 mL) and water (3.5 L). The organic layer is concentrated to dryness. Yield: 1580 g, 97%. Purity: 91% a/a (LC-MS method 2). $^1$H NMR (400 MHz, CDCl3) δ: 7.90 (s, 2H), 7.87 (d, J=8.1 Hz, 1H), 7.34 (d, J=1.6 Hz, 1H), 7.03-7.06 (m, 1H), 2.40 (s, 3H).

The crude product, together with a second batch (1411 g) is purified by distillation on a short path distillation equipment at 120° C. jacket temperature, feeding tank (70° C.), cooling finger (20° C.) and at a pressure of 0.004 mbar. Yield: 2544 g (78%), Purity: 100% a/a ( )LC-MS method 2).

4-Methyl-2-(2H-1,2,3-triazol-2-yl)benzoic acid 2-(2-Iodo-5-methylphenyl)-2H-1,2,3-triazole (1250 g, 1 eq.) is dissolved in THF (13 L) and cooled to 0° C. 2 M iPrMgCl soln. in THF (2.2 L, 1 eq.) is added at 0° C. The mixture is cooled to −25° C. and $CO_2$ (gas) is bubbled into the solution over 60 min until the exothermicity is ceased. To the mixture is added 2 N HCl (5 L) at 4° C. and concentrated under reduced pressure to remove 14.5 L solvent. The residue is extracted with TBME (10 L). The organic layer is extracted with 1N NaOH (6 L and 3 L). The aq. layer is filtered over charcoal (15 g), diluted with water (200 mL) and treated with 32% HCl (1.23 L). The resulting suspension is filtered and washed with water (5 L). Yield: 796 g, 89%. Purity: 100% a/a (LC-MS method 2); MP: 125° C. (DSC goldpan).

The following examples illustrate the invention.

Example 1

Example 1.1: Crystalline 5-methoxy-2-(2H-1,2,3-triazol-2-yl)benzoic acid potassium salt (potassium 5-methoxy-2-(2H-1,2,3-triazol-2-yl)benzoate)

2-Bromo-5-methoxybenzoic acid (21.5 g, 0.093 mol, 1 eq.) copper (I) iodide (0.886 g, 0.05 eq.), and $K_2CO_3$ powder (32.2 g, 2.5 eq.) were suspended in dioxane (600 mL) and water (8.4 mL). To the mixture were added 1H-1,2,3-triazole (10.8 mL, 2 eq.) and trans-N,N-dimethylcyclohexane-1,2-diamine (1.32 g, 0.1 eq.). The mixture was heated at reflux for 3.5 h. IPC showed full conversion. The ratio of the desired N(2) to the regioisomeric N(1) isomer was 84:16. The mixture was cooled to 40° C. and filtered. The cake was washed with dioxane (100 mL). The solid was dried to obtain 50.6 g of a blue solid. The ratio of N(2) to N(1) isomer of was 98.6:1.4.

TABLE 1

| Characterisation data for 5-methoxy-2-(2H-1,2,3-triazol-2-yl)benzoic acid potassium salt in crystalline form 1 | | |
|---|---|---|
| Technique | Data Summary | Remarks |
| XRPD | Crystalline | see FIG. 1 |

Example 1.2: Crystalline 5-methoxy-2-(2H-1,2,3-triazol-2-yl)benzoic acid

The solid of Example 1.1 was dissolved in water (300 mL). TBME (200 mL) and 32% aq. HCl (35 mL) was added. The aq. layer was separated and discarded. The organic layer was washed with a mixture of 2N aq. HCl (100 mL) and 32% aq. HCl (20 mL). The organic layer was washed with 1N aq. HCl (50 mL). The organic layer was extracted with 1N aq. NaOH (200 mL). The aq. layer was heated to 45° C. and traces of TBME were removed under reduced pressure. To the aq. layer was added at 45° C. 32% aq. HCl (20 mL). At a pH of 6 optionally seed crystals were added. The resulting suspension was filtered at 40° C. The cake was washed with water (30 mL). The product was dried at 60° C. and 5 mbar. Yield: 12.4 g, 61%. Purity: 100% a/a, $t_R$ 0.63 min. Seed crystals may be obtained by careful crystallization according to the above procedure.

MP: 80° C. (DSC).

$^1$H NMR (400 MHz, DMSO) δ: 3.87 (s, 3H), 7.26 (m, 2H), 7.64 (d, J=8.7 Hz, 1H), 8.02 (s, 2H), 13.01-13.22 (br, 1H).

TABLE 2

Characterisation data for 5-methoxy-2-(2H-1,2,3-triazol-2-yl)benzoic acid in crystalline form 1

Figure 2:
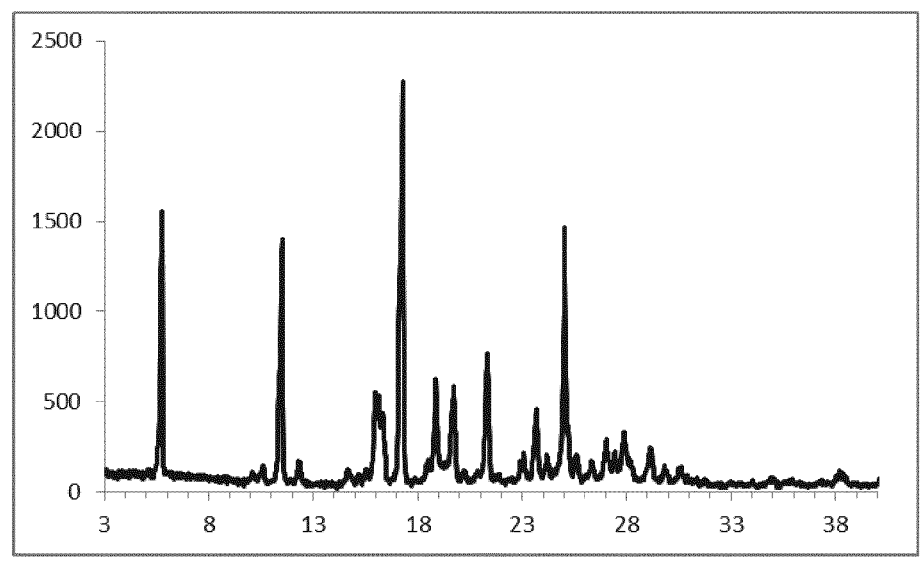
FIG. 2 shows the X-ray powder diffraction diagram of crystalline 5-methoxy-2-(2H-[1,2,3]triazol-2-yl)-benzoic acid as obtained from Example 1.2. The X-ray diffraction diagram measured with method 2 shows peaks having a relative intensity, as compared to the most intense peak in the diagram, of the following percentages (relative peak intensitites given in parenthesis) at the indicated angles of refraction 2theta (selected peaks from the range 3-40° 2theta are reported): 5.7° (66%), 11.5° (66%), 16.0° (24%), 16.1° (20%), 16.3° (19%), 17.2° (100%), 18.9° (29%), 19.7° (25%), 21.3° (37%), 23.7° (19%), 25.0° (75%), 27.0° (12%), 27.9° (14%).

| Technique | Data Summary | Remarks |
|---|---|---|
| XRPD | Crystalline | see FIG. 2 |

Example 1.3: Crystalline 5-methoxy-2-(2H-1,2,3-triazol-2-yl)benzoic acid potassium salt 5-Methoxy-2-(2H-1,2,3-triazol-2-yl)benzoic acid, e.g. obtained according to the procedure of Reference Example 1 (5 g, 0.0228 mol) and KHCO$_3$ (1.61 g, 0.7 eq) were suspended in dioxane (100 mL) and water (1 mL). The mixture was heated at reflux for 40 min. The mixture was cooled to 20° C. and filtered. Yield: 2.56 g, 44%. $^1$H NMR (400 MHz, D2O) δ: 3.80 (s, 3H), 7.04 (m, 2H), 7.46 (d, J=8.7 Hz, 1H), 7.82 (s, 2H). MP: 279.5° C. (DSC shows additionally a broad endothermic event at about 153° C. to 203° C. which may be attributed to endothermic desolvations; melting is immediately followed by exothermic degradation).

TABLE 3

Characterisation data for 5-methoxy-2-(2H-1,2,3-triazol-2-yl)benzoic acid potassium salt in crystalline form 2

Figure 3:
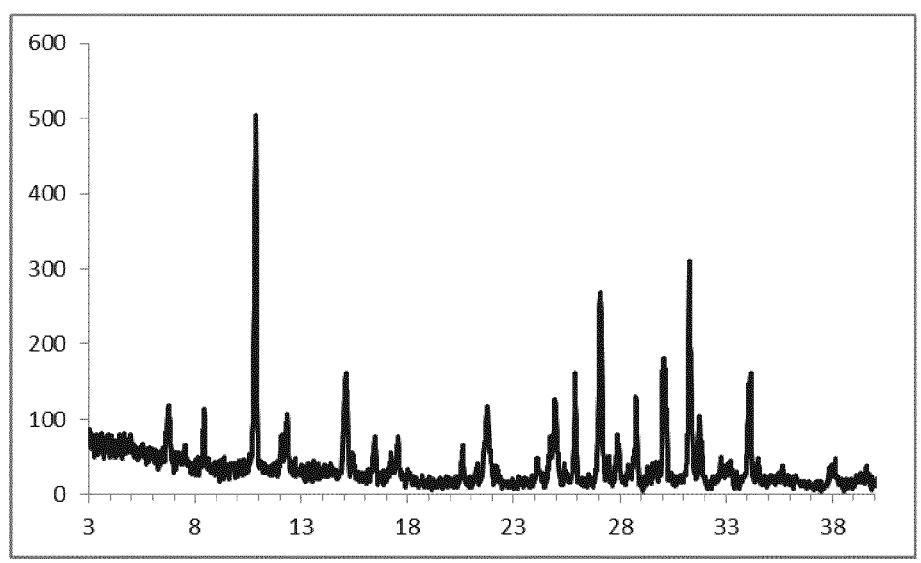
FIG. 3 shows the X-ray powder diffraction diagram of crystalline 5-methoxy-2-(2H-[1,2,3]triazol-2-yl)-benzoic acid potassium salt, the compound of Example 1.3. The X-ray diffraction diagram shows peaks having a relative intensity, as compared to the most intense peak in the diagram, of the following percentages (relative peak intensitites given in parenthesis) at the indicated angles of refraction 2theta (selected peaks from the range 3-40° 2theta are reported): 6.7° (15%), 8.4° (19%), 10.8° (100%), 12.3° (15%), 15.1° (33%), 16.4° (11%), 17.5° (12%), 20.6° (10%), 21.8° (24%), 24.7° (14%), 25.0° (25%), 25.9° (35%), 27.1° (63%), 27.9° (12%), 28.8° (29%).

| Technique | Data Summary | Remarks |
|---|---|---|
| XRPD | Crystalline | see FIG. 3 |

Example 1.4: Crystalline 5-methoxy-2-(2H-1,2,3-triazol-2-yl)benzoic acid potassium salt In an alternative procedure, 2-Bromo-5-methoxybenzoic acid (20 g, 0.086 mol, 1 eq.) copper (I) iodide (0.824 g, 0.05 eq.), and K$_2$CO$_3$ powder (26.9 g, 2.25 eq.) were suspended in dioxane (494 mL). To the mixture was added 1H-1,2,3-triazole (12 g, 2 eq.). The mixture was heated at reflux for 1 h. To the mixture was added water (12.5 g, 8 eq.). The mixture was heated at reflux for 2 h. Solvent (100 mL) was removed by distillation. The residue was cooled to 45° C. in 8 min, filtered and washed with dioxane (50 mL).

XRPD corresponds to crystalline form 1 (see FIG. 1, Example 1.1).

Example 1.5: Crystalline 5-methoxy-2-(2H-1,2,3-triazol-2-yl)benzoic acid

The solid of Example 1.4 was dissolved in water (200 mL). The mixture was heated to 50° C. and 20% aq. H$_2$SO$_4$ (40 mL) was added to adjust the pH to 5. The mixture was filtered over Celite. The filtrate was treated at 45° C. with 20% aq. H$_2$SO$_4$ (40 mL). At pH 3 seeds (obtained for example using the procedure of reference example 1) were added. The suspension was stirred at 45° C. and filtered. The product was washed with water (20 mL) and dried at 60° C. and 10 mbar to yield a white solid. Yield: 10.8 g, 57%. Purity: 100% a/a, $t_R$ 0.63 min.

Characterisation of 5-methoxy-2-(2H-1,2,3-triazol-2-yl)benzoic acid obtained according to Example 1.5:

XRPD corresponds to crystalline form 1 (see FIG. 2, Example 1.2).

Example 2

Example 2.1: Crystalline 4-methyl-2-(2H-1,2,3-triazol-2-yl)benzoic acid potassium salt (potassium 4-methyl-2-(2H-1,2,3-triazol-2-yl)benzoate)

2-Bromo-4-methylbenzoic acid (20 g, 0.093 mol, 1 eq.) copper (I) iodide (0.886 g, 0.05 eq.), and K$_2$CO$_3$ powder (32.2 g, 2.5 eq.) were suspended in dioxane (300 mL) and water (10.1 mL). To the mixture was added 1H-1,2,3-triazole (10.8 mL, 2 eq.) and trans-N,N-dimethylcyclohexane-1,2-diamine (1.32 g, 0.1 eq.). The mixture was heated at reflux for 4 h. IPC showed a conversion of 98.5%. The ratio of the desired N(2) to the regioisomeric N(1) isomer was 75:25. The mixture was concentrated at normal pressure and external temperature of 130° C. Solvent (100 mL) was removed. To the residue was added dioxane (100 mL) and the mixture was cooled to 45° C. and filtered. The cake was washed with dioxane (80 mL). The solid was dried to obtain 48.8 g of a blue solid. The ratio of N(2) to N(1) isomer was 98.7-1.3.

TABLE 4

Characterisation data for 4-methyl-2-(2H-1,2,3-triazol-2-yl)benzoic acid potassium salt in crystalline form 1

Figure 4:
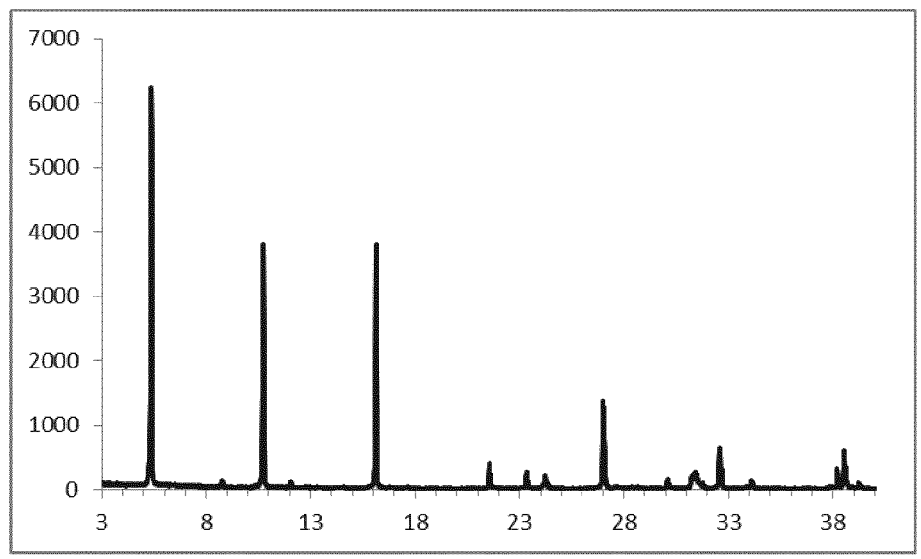
FIG. 4 shows the X-ray powder diffraction diagram of crystalline 4-methyl-2-(2H-[1,2,3]triazol-2-yl)-benzoic acid potassium salt, the compound of Example 2.1. The X-ray diffraction diagram shows peaks having a relative intensity, as compared to the most intense peak in the diagram, of the following percentages (relative peak intensitites given in parenthesis) at the indicated angles of refraction 2theta (selected peaks from the range 3-40° 2theta are reported): 5.4° (100%), 8.8° (1%), 10.7° (56%), 12.0° (1%), 16.1° (60%), 21.6° (5%), 23.3° (4%), 24.2° (3%), 27.0° (21%), 32.6° (8%).

| Technique | Data Summary | Remarks |
|---|---|---|
| XRPD | Crystalline | see FIG. 4 |

Example 2.2: Crystalline 4-methyl-2-(2H-1,2,3-triazol-2-yl)benzoic acid

The solid of Example 2.1 was dissolved in water (300 mL) and filtered. To the filtrate were added TBME (200 mL) and 32% aq. HCl (30 mL). The aq. layer was separated and discarded. The organic layer was washed with a mixture of 2N aq. HCl (100 mL) and 32% aq. HCl (10 mL). The organic layer was washed with 1N aq. HCl (50 mL). The organic layer was extracted with 1N aq. NaOH (200 mL). The aq. layer was heated to 45° C. and traces of TBME were removed under reduced pressure. To the aq. layer was added at 45° C. 32% aq. HCl (20 mL). At a pH of 6 seed crystals (obtained for example using the procedure of reference example 2) were added. The resulting suspension was filtered at 40° C. The cake was washed with water (30 mL). The product was dried at 60° C. and 5 mbar. Yield: 11.7 g, 62%. Purity: 100% a/a. $t_R$ 0.66 min.

MP: 125° C. (DSC).

$^1$H NMR (400 MHz, DMSO) δ: 2.44 (s, 3H), 7.41 (d, J=7.9 Hz, 1H), 7.56 (s, 1H), 7.68 (d, J=7.9 Hz, 1H), 8.06 (s, 2H), 12.53-13.26 (br, 1H)

TABLE 5

Characterisation data for 4-methyl-2-(2H-1,2,3-triazol-2-yl)benzoic acid in crystalline form 1

Figure 5:
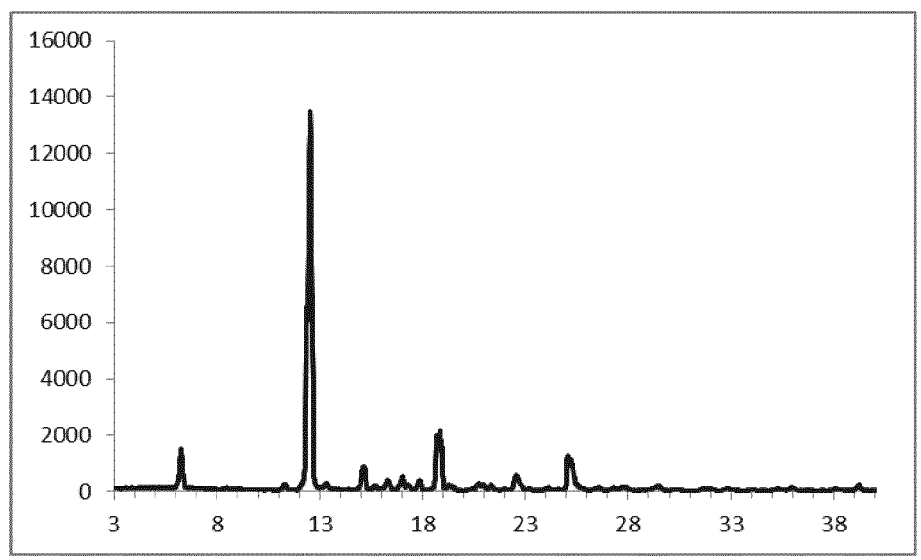
FIG. 5 shows the X-ray powder diffraction diagram of crystalline 4-methyl-2-(2H-[1,2,3]triazol-2-yl)-benzoic acid as obtained from Example 2.2. The X-ray diffraction diagram measured with method 2 shows peaks having a relative intensity, as compared to the most intense peak in the diagram, of the following percentages (relative peak intensitites given in parenthesis) at the indicated angles of refraction 2theta (selected peaks from the range 3-40° 2theta are reported): 6.2° (11%), 11.3° (2%), 12.5° (100%), 13.3° (2%), 15.1° (7%), 17.0° (4%), 17.8° (3%), 18.8° (15%), 22.6° (4%), 25.2° (8%).

| Technique | Data Summary | Remarks |
| --- | --- | --- |
| XRPD | Crystalline | see FIG. 5 |

Example 2.3: Crystalline 4-methyl-2-(2H-1,2,3-triazol-2-yl)benzoic acid potassium salt 4-Methyl-2-(2H-1,2,3-triazol-2-yl)benzoic acid (5 g, 0.0246 mol) and KHCO$_3$ (1.74 g, 0.7 eq) were suspended in dioxane (100 mL) and water (1 mL). The mixture was heated at reflux for 40 min. The mixture was cooled to 20° C. and filtered. Yield: 2.47 g, 42%. MP: 277° C. (DSC Alupan) $^1$H NMR (400 MHz, D2O) δ: 2.32 (s, 3H), 7.28 (d, J=7.9 Hz, 1H), 7.39 (m, 2H), 7.84 (s, 2H).

MP: 276.8° C. (DSC shows additionally a broad endothermic event at about 140° C. to 208° C. which may be attributed to endothermic desolvations; melting is immediately followed by exothermic degradation).

XRPD corresponds to crystalline form 1 (see FIG. 4, Example 2.1).

Reference Example 3

Reference Example 3.1: Crystalline 5-methyl-2-(2H-1,2,3-triazol-2-yl)benzoic acid sodium salt (sodium 5-methyl-2-(2H-1,2,3-triazol-2-yl)benzoate)

2-Bromo-5-methylbenzoic acid (20 g, 0.093 mol, 1 eq.) copper (I) iodide (0.886 g, 0.05 eq.), Na$_2$CO$_3$ powder (24.6 g, 2.5 eq.) were suspended in dioxane (300 mL) and water (10.1 mL). To the mixture was added 1H-1,2,3-triazole (10.8 mL, 2 eq.) and 8-hydroxy quinoline (1.35 g, 0.1 eq.). The mixture was heated at reflux for 5 h. IPC showed a conversion of >99%. The ratio of the desired N(2) to the regioisomeric N(1) isomer was 78:22. The mixture was concentrated at normal pressure and external temperature of 135° C. Solvent (100 mL) was removed. To the residue was added dioxane (100 mL) and the mixture was cooled to 45° C. and filtered. The cake was washed with dioxane (80 mL). The solid was dried to obtain 36.2 g of a yellow solid. The ratio of N(2) to N(1) isomer of was 99:1.

TABLE 6

Characterisation data for 5-methyl-2-(2H-1,2,3-triazol-2-yl)benzoic acid sodium salt in crystalline form 1

Figure 6:
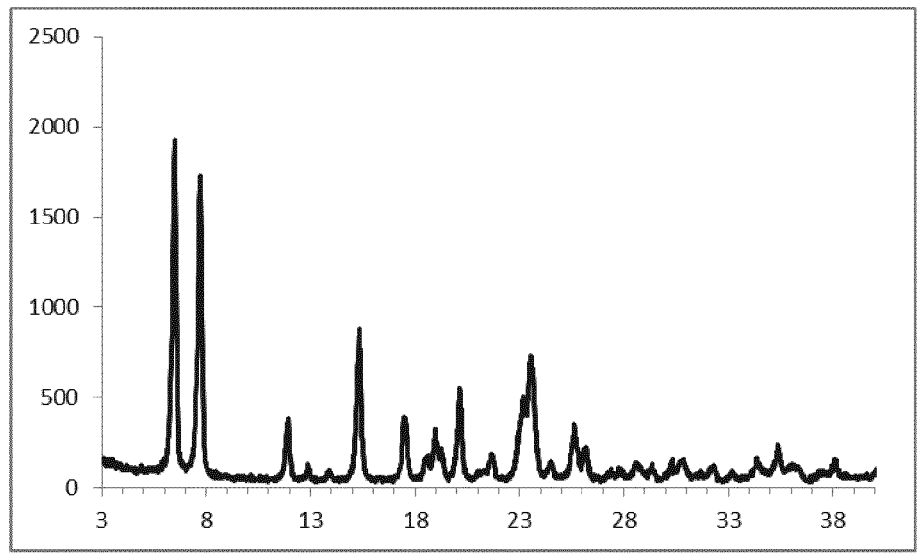
FIG. 6 shows the X-ray powder diffraction diagram of crystalline 5-methyl-2-(2H-[1,2,3]triazol-2-yl)-benzoic acid sodium salt, the compound of Reference Example 3.1. The X-ray diffraction diagram measured with method 2 shows peaks having a relative intensity, as compared to the most intense peak in the diagram, of the following percentages (relative peak intensitites given in parenthesis) at the indicated angles of refraction 2theta (selected peaks from the range 3-40° 2theta are reported): 6.5° (100%), 7.7° (91%), 11.9° (18%), 12.9° (5%), 13.9° (3%), 15.3° (47%), 17.5° (20%), 18.6° (6%), 19.0° (13%), 19.2° (9%), 20.1° (28%), 21.7° (7%), 23.2° (24%), 23.6° (38%), 24.5° (5%), 25.6° (17%).

| Technique | Data Summary | Remarks |
| --- | --- | --- |
| XRPD | Crystalline | see FIG. 6 |

Reference Example 3.2: Crystalline 5-methyl-2-(2H-1,2,3-triazol-2-yl)benzoic acid The solid obtained in Reference Example 3.1 was dissolved in water (300 mL) and filtered. To the filtrate was added TBME (200 mL) and 32% aq. HCl (30 mL) was added. The aq. layer was separated and discarded. The organic layer was washed with 1N aq. HCl (100 mL). The organic layer was washed with 1N aq. HCl (50 mL). The organic layer was extracted with 1N aq. NaOH (200 mL). The aq. layer was heated to 45° C. and traces of TBME were removed under reduced pressure. To the aq. layer was added at 45° C. 32% aq. HCl (20 mL). At a pH of 6 seed crystals (obtained for example using the procedure of Reference example 2) were added. The resulting suspension was filtered at 40° C. The cake was washed with water (30 mL). The product was dried at 60° C. and 5 mbar. Yield: 12.1 g, 64%. Purity: 100% a/a. $t_R$0.67 min.

MP: 173° C. (DSC)

$^1$H NMR (400 MHz, DMSO) δ: 2.42 (s, 3H), 7.50-7.52 (m, 1H), 7.58 (s, 1H), 7.63 (m, 1H), 8.05 (s, 2H), 13.01 (s, 1H).

TABLE 7

Characterisation data for 5-methyl-2-(2H-1,2,3-triazol-2-yl)benzoic acid in crystalline form 1

Figure 7:
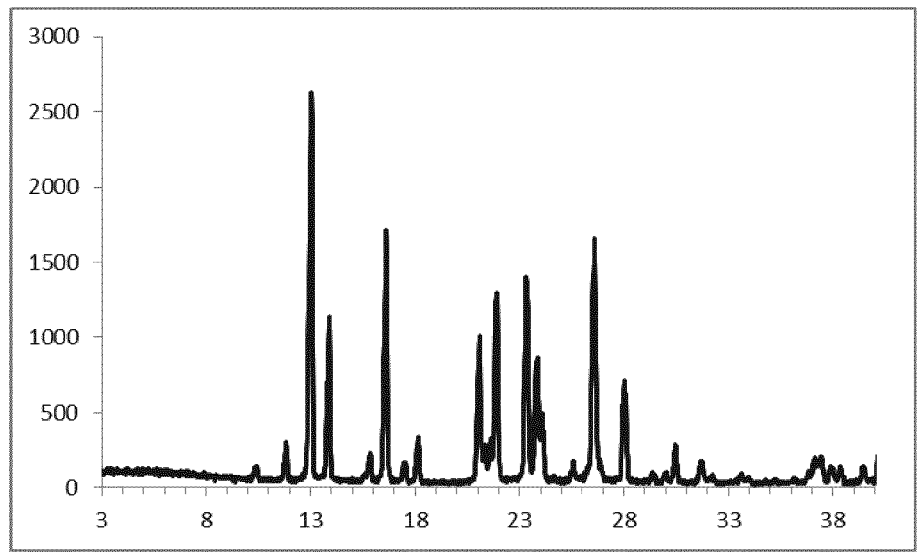
FIG. 7 shows the X-ray powder diffraction diagram of crystalline 5-methyl-2-(2H-[1,2,3]triazol-2-yl)-benzoic acid, the compound of Reference Example 3.2. The X-ray diffraction diagram measured with method 2 shows peaks having a relative intensity, as compared to the most intense peak in the diagram, of the following percentages (relative peak intensitites given in parenthesis) at the indicated angles of refraction 2theta (selected peaks from the range 3-40° 2theta are reported): 10.4° (3%), 11.8° (10%), 13.0° (100%), 13.9° (44%), 15.8° (8%), 16.6° (74%), 17.5° (5%), 18.1° (13%), 21.1° (41%), 21.3° (10%), 21.6° (12%), 21.9° (58%), 23.3° (62%), 23.8° (37%), 24.1° (16%), 24.6° (1%), 25.6° (6%), 26.6° (71%), 28.0° (32%), 29.4° (3%), 30.0° (2%), 30.5° (11%).

| Technique | Data Summary | Remarks |
| --- | --- | --- |
| XRPD | Crystalline | see FIG. 7 |

Reference Example 3.3: Crystalline 5-methyl-2-(2H-1,2,3-triazol-2-yl)benzoic acid sodium salt 5-Methyl-2-(2H-1,2,3-triazol-2-yl)benzoic acid (5 g, 0.0246 mol) and Na$_2$CO$_3$ (1.05 g, 0.4 eq) were suspended in dioxane (100 mL) and water (1 mL). The mixture was heated at reflux for 40 min. The mixture was cooled to 20° C. and filtered. Yield: 2.79 g, 50%. MP: 341° C. (DSC Alupan) $^1$H NMR (400 MHz, D2O) δ: 5.2.32 (s, 3H), 7.30 (m, 2H), 7.43 (m, 1H), 7.83 (s, 2H). XRPD corresponds to crystalline form 1 (see FIG. 6, Reference Example 3.1).

Reference Example 3.4: 5-methyl-2-(2H-1,2,3-triazol-2-yl)benzoic acid potassium Salt 2-Bromo-5-methylbenzoic acid (20 g, 0.093 mol, 1 eq.) copper (I) iodide (0.886 g, 0.05 eq.), and K$_2$CO$_3$ powder (32.1 g, 2.5 eq.) were suspended in dioxane (600 mL). To the mixture was added 1H-1,2,3-triazole (10.8 mL, 2 eq.) and 8-hydroxy quinoline (1.35 g, 0.1 eq.). The mixture was heated at reflux for 4 h. IPC showed a conversion of >94%. The ratio of the desired N(2) to the regioisomeric N(1) isomer was 78:22. The mixture was cooled to 35° C. and filtered. The cake was washed with dioxane (100 mL). The products were dissolved in water and a LC-MS was recorded. The ratio of N(2) to N(1) isomer of was 83:17.

Reference Example 4.1: Methyl (S)-1-(5-methoxy-2-(2H-1,2,3-triazol-2-yl) benzoyl)-2-methylpyrrolidine-2-carboxylate 5-Methoxy-2-(2H-1,2,3-triazol-2-yl) benzoic acid (100 g, 0.46 mol) was suspended in DCM (650 mL) and DMF (10 mL) at 20° C. To this suspension was added oxalyl chloride (51 mL, 0.59 mol) over a period of 30 min. LC-MS showed 60% conversion to acid chloride intermediate. Oxalyl chloride (17.6 mL, 0.45 eq.) was added dropwise. LC-MS showed full conversion to acid chloride intermediate.

Methyl (S)-2-methylpyrrolidine-2-carboxylate hydrochloride (84 g, 0.47 mol) was suspended in DCM (800 mL) in a second flask. The suspension was cooled to 10° C. Triethylamine (200 mL, 1.41 mol) was added over 15 min. The acid chloride solution was added to the reaction mixture at 10-20° C. over at least 15 min. The reaction mixture was washed with 1M HCl (500 mL), 1N NaOH (500 mL) and water (500 mL). The organic layer was concentrated to dryness to give a light-yellow solid as product. Yield: 157 g, 100%, 99% a/a (LC-MS), M+1=345.

$^1$H NMR (400 MHz, DMSO) δ: 8.06 (s, 2H), 7.79 (d, J=8.9 Hz, 1H), 7.21 (dd, J1=2.9 Hz, J2=8.9 Hz, 1H), 6.85 (d, J=1.9 Hz, 1H), 3.89 (s, 3H), 3.66 (s, 3H), 3.29 (m, 1H), 3.03 (m, 1H), 2.08 (m, 1H), 1.82 (m, 3H), 1.50 (s, 3H).

Reference Example 4.2: (S)-1-(5-methoxy-2-(2H-1,2,3-triazol-2-yl) benzoyl)-2-methylpyrrolidine-2-carboxylic acid Methyl (S)-1-(5-methoxy-2-(2H-1,2,3-triazol-2-yl) benzoyl)-2-methylpyrrolidine-2-carboxylate (157 g, 0.46 mol) was dissolved in MeOH (750 mL) at 20° C. To this solution was added 16% NaOH (300 mL). The resulting solution was heated up to 80° C. and stirred for 60 min. Solvent was distilled off under reduced pressure (850 mL). The residue was taken up in DCM (1500 mL) and water (450 ml) at 20° C. 32% HCl (200 mL) was added. Layers were separated and the organic layer was washed with water (450 mL). The organic layer was concentrated to the minimum stirring volume under reduced pressure. Toluene (750 mL) was added and solvent was further distilled under vacuum (150 mL distilled). The mixture was cooled to 20° C. and stirred for 15 min. The suspension was filtered at 20° C. The cake was rinsed with toluene (150 mL) and then dried under reduced pressure at 50° C. to give a white solid as product. Yield: 128 g, 85%, 94% a/a (LC-MS), M+1=331. Melting point: 178° C. (DSC). $^1$H NMR (400 MHz, DMSO) δ: 12.3 (s, 1H), 8.04 (s, 2H), 7.79 (d, 1H), 7.20 (dd, J1=2.8 Hz, J2=8.9 Hz, 1H), 6.84 (m, 1H), 3.88 (s, 3H), 3.29 (m, 1H), 2.99 (m, 1H), 2.11 (m, 1H), 1.81 (m, 3H), 1.47 (s, 3H).

Reference Example 4.3: (S)—N-(2-amino-4-chloro-3-methylphenyl)-1-(5-methoxy-2-(2H-1,2,3-triazol-2-yl) benzoyl)-2 methylpyrrolidine-2-carboxamide (S)-1-(5-Methoxy-2-(2H-1,2,3-triazol-2-yl) benzoyl)-2-methylpyrrolidine-2-carboxylic acid (128 g, 0.39 mol) was suspended in DCM (850 mL) and DMF (6 mL) at 20° C. To this suspension was added oxalyl chloride (39 mL, 0.45 mol) over a period of 30 min. 4-Chloro-3-methylbenzene-1,2-diamine hydrochloride (75 g, 0.39 mol) was suspended in DCM (1300 mL) in a second flask. The suspension was cooled down to 10° C. Triethylamine (180 mL, 1.27 mol) was added. The acid chloride solution was added to the reaction mixture at 10-20° C. over at least 15 min. Water (650 mL) was added to the reaction mixture. Layers were separated and the organic phase was concentrated under reduced pressure (1900 mL distilled out). TBME (1000 mL) was added and solvent was further distilled under vacuum (400 mL distilled). The mixture was finally cooled down to 20° C. and stirred for 15 min. The resulting suspension was filtered off at 20° C. The cake was rinsed with TBME (250 mL) and then dried under reduced pressure at 50° C. to give a white solid as product. Yield: 145 g, 80%, 97% a/a (LC-MS), M+1=469. Melting point: 185° C. (DSC). $^1$H NMR (400 MHz, DMSO) δ: 9.10-9.14 (m, 1H), 7.88-8.12 (m, 2H), 7.81-7.82 (m, 1H), 7.38-7.44 (m, 1H), 7.21 (dd, J1=2.7 Hz, J2=8.9 Hz, 1H), 6.84 (d, J=7.8 Hz, 1H), 6.64 (d, J=8.3 Hz, 1H), 5.01 (brs, 2H), 3.88 (s, 3H), 3.61-3.73 (m, 1H), 3.14-3.26 (m, 1H), 2.25-2.30 (m, 1H), 2.13 (s, 3H), 1.97 (m, 3H), 1.47-1.61 (m, 3H).

Reference Example 4.4: (S)-(2-(5-chloro-4-methyl-1H-benzo[d]imidazol-2-yl)-2-methylpyrrolidin-1-yl) (5-methoxy-2-(2H-1,2,3-triazol-2-yl)phenyl)methanone hydrochloride (S)—N-(2-amino-4-chloro-3-methylphenyl)-1-(5-methoxy-2-(2H-1,2,3-triazol-2-yl) benzoyl)-2 methylpyrrolidine-2-carboxamide (145 g, 0.31 mol) was dissolved in isopropanol (870 mL) at 20° C. To this solution was added carefully 5-6 N HCl in isopropanol (260 mL) over 10 min. the reaction mixture was then heated up to 90° C. and stirred for 4 hours. Water (28 mL) was added and the reaction mixture was stirred for an additional one hour. The reaction mixture was cooled to 20° C. A light brown suspension was obtained which was filtered. The cake was rinsed with isopropanol (220 mL). The solid was finally dried under reduced pressure at 60° C. to give a beige solid. Yield: 133 g, 88%, 100% a/a (LC-MS), M+1=451. Melting point: 277° C. (DSC). $^1$H NMR (400 MHz, DMSO) δ: 8.06 (s, 2H), 7.76 (d, J=8.9 Hz, 1H), 7.63 (d, J=8.8 Hz, 2H), 7.55 (m, 1H), 7.16 (dd, J1=2.7 Hz, J2=8.9 Hz, 1H), 3.98 (m, 1H), 3.90 (s, 3H), 3.33 (m, 2H), 3.32 (m, 1H), 2.74 (s, 3H), 2.55 (m, 1H), 2.23 (m, 1H), 2.10 (m, 2H), 1.95 (s, 3H).

The invention claimed is:

1. A process for the synthesis of a crystalline potassium salt of a 2-(2H-[1,2,3]triazol-2-yl)-benzoic acid derivative of Formula ($I_K$):

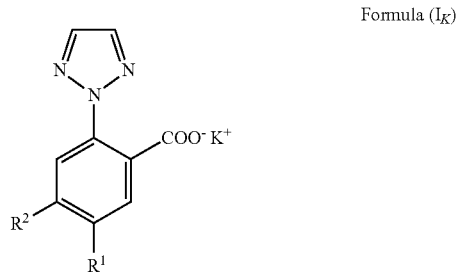

Formula ($I_K$)

wherein
$R^1$ represents methoxy and $R^2$ represents hydrogen; or
$R^1$ represents hydrogen and $R^2$ represents methyl;
said process comprising the coupling of
a compound of Formula (II):

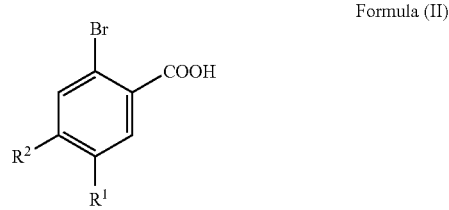

Formula (II)

and [1,2,3]triazole:

wherein said process is conducted in the presence of:
- copper (I) iodide (CuI);
- an inorganic potassium base; and
- a solvent or solvent mixture which is
  - a water miscible ether solvent; or
  - a polar aprotic solvent;
  - or any mixture thereof;
    - wherein said solvent or solvent mixture is present in an amount of about 5 to 100 vol with respect to the compound of Formula (II);
- wherein said coupling of the compound of Formula (II) and [1,2,3]triazole is performed at a temperature of greater than about 60° C.;
- wherein said crystalline compound of Formula ($I_K$) is isolated from the reaction mixture by solid-liquid separation.

2. The process according to claim 1, wherein said process is conducted in the presence of Cu (I) iodide; wherein Cu (I) iodide is present in an amount of about 0.01 eq. to 0.5 eq. with respect to the compound of Formula (II).

3. The process according to claim 2, wherein said inorganic potassium base is $K_2CO_3$; wherein $K_2CO_3$ is present in an amount of about 1 eq. to 10 eq. with respect to the compound of Formula (II).

4. The process according to claim 3, wherein 1H-1,2,3-triazole is present in an amount of about 1 eq. to 10 eq. with respect to the compound of Formula (II).

5. The process according to claim 4, wherein said process is conducted in presence of
- a solvent which is a water miscible ether solvent; wherein said water miscible ether solvent is present in an amount of about 5 to 100 vol with respect to the compound of Formula (II); and
- water in an amount of about 0.05 to 2 vol with respect to the compound of Formula (II);
- wherein the ratio of water miscible ether solvent to water greater than about 10:1 (v/v).

6. The process according to claim 5, wherein, prior to the isolation of the crystalline compound of Formula ($I_K$) from the reaction mixture by solid-liquid separation, said the reaction mixture is cooled to a temperature of below about 50° C.; and wherein said cooling of the reaction mixture is achieved within about 2 hours or less.

7. The process according to claim 1, wherein said isolated crystalline compound of Formula ($I_K$):

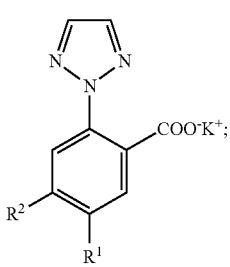

Formula ($I_K$)

wherein
- $R^1$ represents methoxy and $R^2$ represents hydrogen; or
- $R^1$ represents hydrogen and $R^2$ represents methyl;

is further transformed into the respective crystalline 2-(2H-[1,2,3]triazol-2-yl)-benzoic acid derivative of Formula (I):

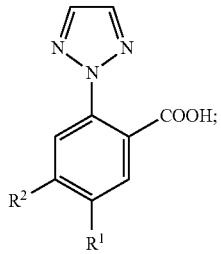

Formula (I)

said process comprising a crystallization step from acidic aqueous medium.

8. The process according to claim 7, wherein said crystallization step from acidic aqueous medium is performed at a temperature of about 30° C. to 60° C.; and wherein said crystalline compound of Formula (I) is isolated by solid-liquid separation; wherein said solid-liquid separation is performed at a temperature of about 10° C. to 50° C.

9. The process according to claim 8, wherein, in the crystallization step from acidic aqueous medium, said acidic aqueous solution has a pH of below about 4.

10. A crystalline form of the compound of Formula ($I_K$):

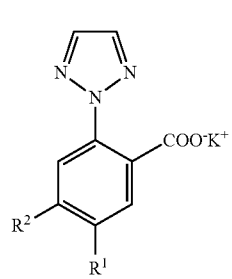

Formula ($I_K$)

wherein $R^1$ represents methoxy and $R^2$ represents hydrogen; characterized by:
- a) the presence of peaks in the X-ray powder diffraction diagram at the following angles of refraction 2θ: 6.7°, 7.4°, 15.4°, 23.3°, 27.0°; or
- b) the presence of peaks in the X-ray powder diffraction diagram at the following angles of refraction 2θ: 10.8°, 15.1°, 25.0°, 25.9°, 27.1°;
- or wherein $R^1$ represents hydrogen and $R^2$ represents methyl;
- characterized by the presence of peaks in the X-ray powder diffraction diagram at the following angles of refraction 2θ: 5.4°, 10.7°, 16.1°, 21.6°, 27.0°;
- wherein said X-ray powder diffraction diagram is obtained by using combined Cu Kα1 and Kα2 radiation, without Kα2 stripping; and the accuracy of the 2θ values is in the range of 2θ+/−0.2°.

11. A crystalline form of the compound of Formula (I):

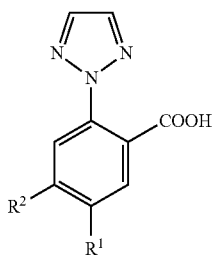

Formula (I)

wherein R¹ represents methoxy and R² represents hydrogen;
   a) characterized by the presence of peaks in the X-ray powder diffraction diagram at the following angles of refraction 2θ: 5.7°, 11.5°, 17.2°, 21.3°, 25.0°; or
   b) characterized by the presence of peaks in the X-ray powder diffraction diagram at the following angles of refraction 2θ: 11.4°, 12.3°, 15.5°, 21.3°, 23.6°;
or wherein R¹ represents hydrogen and R² represents methyl;
characterized by the presence of peaks in the X-ray powder diffraction diagram at the following angles of refraction 2θ: 6.2°, 12.5°, 15.1°, 18.8°, 25.2°; wherein said X-ray powder diffraction diagram is obtained by using combined Cu Kα1 and Kα2 radiation, without Kα2 stripping; and the accuracy of the 2θ values is in the range of 2θ+/−0.2°.

12. The process according to claim 1, wherein said process is conducted in the presence of Cu (I) iodide; wherein Cu (I) iodide is present in an amount of about 0.01 eq. to 0.1 eq. with respect to the compound of Formula (II).

13. The process according to claim 1, wherein said inorganic potassium base is $K_2CO_3$, $K_3PO_4$ or $KHCO_3$.

14. The process according to claim 1, wherein said inorganic potassium base is $K_2CO_3$.

15. The process according to claim 1, wherein said inorganic potassium base is $K_2CO_3$; wherein $K_2CO_3$ is present in an amount of about 1.5 eq. to 5 eq. with respect to the compound of Formula (II).

16. The process according to claim 1, wherein said water miscible ether solvent is tetrahydrofurane (THF), 2-methyl-THF, 1,4-dioxane, or 1,2-dimethoxyethane; and said polar aprotic solvent is dimethylformamide (DMF), dimethylacetamide, or N-methylpyrrolidin-2-one (NMP); wherein said solvent or solvent mixture is present in an amount of about 5 to 100 vol with respect to the compound of Formula (II).

17. The process according to claim 1, wherein said solvent is 1,4-dioxane.

18. The process according to claim 17, wherein said solvent is present in an amount of about 10 to 50 vol with respect to the compound of Formula (II).

19. The process according to claim 1, wherein said process:
   is conducted in the presence of a ligand which is 8-hydroxyquinoline, N1,N2-dimethylcyclohexan-1,2-diamine, or N,N-dimethyl-ethylene-diamine; wherein said ligand is present in an amount of about 0.01 eq. to 0.5 eq. with respect to the compound of Formula (II); or
   is conducted in absence of a ligand.

20. The process according to claim 1, wherein 1H-1,2,3-triazole is present in an amount of about 1.5 eq. to 5 eq. with respect to the compound of Formula (II).

21. The process according to claim 1, wherein isolation of said crystalline compound of Formula ($I_K$) from the reaction mixture by solid-liquid separation leads to the crystalline potassium salt in a regioisomeric ratio of greater than about 90:10.

22. The process according to claim 5, wherein said inorganic potassium base is $K_2CO_3$; wherein $K_2CO_3$ is present in an amount of about 1.5 eq. to 5 eq. with respect to the compound of Formula (II).

23. The process according to claim 5, wherein said solvent is 1,4-dioxane.

24. The process according to claim 5, wherein said water miscible ether solvent is present in an amount of about 10 to 50 vol with respect to the compound of Formula (II).

25. The process according to claim 5, wherein the ratio of water miscible ether solvent to water is about 10:1 to 200:1 (v/v).

26. The process according to claim 5, wherein the ratio of water miscible ether solvent to water is about 20:1 to 100:1 (v/v).

27. The process according to claim 5, wherein prior to the isolation of the crystalline compound of Formula ($I_K$) from the reaction mixture by solid-liquid separation, the amount of water in the reaction mixture is reduced; and wherein subsequently further water miscible ether solvent is added to the reaction mixture.

28. The process according to claim 27, wherein said inorganic potassium base is $K_2CO_3$; wherein $K_2CO_3$ is present in an amount of about 1.5 eq. to 5 eq. with respect to the compound of Formula (II).

29. The process according to claim 27, wherein said solvent is 1,4-dioxane.

30. The process according to claim 27, wherein said ratio of water miscible ether solvent to water is about 10:1 to 200:1 (v/v).

31. The process according to claim 7, wherein said process comprises the steps:
   (i) preparing a basic aqueous solution comprising the compound of Formula (I);
   (ii) crystallizing said compound of Formula (I) by acidifying said basic aqueous solution comprising said compound of Formula (I); and
   (iii) isolating said crystalline compound of Formula (I) by solid-liquid separation.

32. The process according to claim 9, wherein, in said crystallization step, an aqueous inorganic acid solution is used to acidify said basic aqueous solution.

33. The process according to claim 32, wherein said aqueous inorganic acid solution is aqueous sulfuric acid, or aqueous hydrochloric acid.

34. A crystalline form of the compound of Formula ($I_K$):

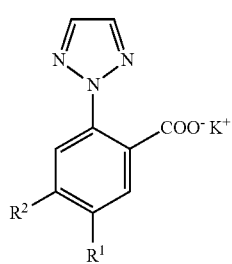

Formula ($I_K$)

wherein R¹ represents methoxy and R² represents hydrogen; characterized by the presence of peaks in the X-ray powder diffraction diagram at the following angles of refraction 2θ: 6.7°, 7.4°, 15.4°, 23.3°, 27.0°; wherein said X-ray powder diffraction diagram is obtained by using combined Cu Kα1 and Kα2 radiation, without Kα2 stripping; and the accuracy of the 2θ values is in the range of 2θ+/−0.2°.

35. The crystalline form of the compound of Formula ($I_K$) according to claim 34, characterized by the presence of peaks in the X-ray powder diffraction diagram at the following angles of refraction 2θ: 6.7°, 7.4°, 8.7°, 15.4°, 16.4°, 20.2°, 23.3°, 24.4°, 27.0°, 28.1°; wherein said X-ray powder diffraction diagram is obtained by using combined Cu Kα1 and Kα2 radiation, without Kα2 stripping; and the accuracy of the 2θ values is in the range of 2θ+/−0.2°.

36. A crystalline form of the compound of Formula ($I_K$):

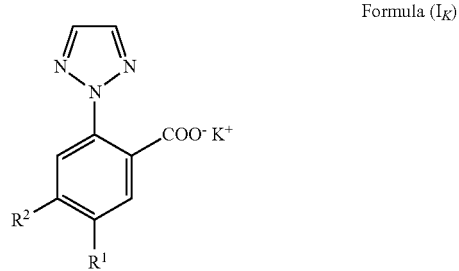

Formula ($I_K$)

wherein R¹ represents methoxy and R² represents hydrogen; characterized by the presence of peaks in the X-ray powder diffraction diagram at the following angles of refraction 2θ: 10.8°, 15.1°, 25.0°, 25.9°, 27.1°; wherein said X-ray powder diffraction diagram is obtained by using combined Cu Kα1 and Kα2 radiation, without Kα2 stripping; and the accuracy of the 2θ values is in the range of 2θ+/−0.2°.

37. The crystalline form of the compound of Formula ($I_K$) according to claim 36, characterized by the presence of peaks in the X-ray powder diffraction diagram at the following angles of refraction 2θ: 8.4°, 10.8°, 12.3°, 15.1°, 17.5°, 25.0°, 25.9°, 27.1°, 27.9°, 28.8°; wherein said X-ray powder diffraction diagram is obtained by using combined Cu Kα1 and Kα2 radiation, without Kα2 stripping; and the accuracy of the 2θ values is in the range of 2θ+/−0.2°.

38. A crystalline form of the compound of Formula ($I_K$):

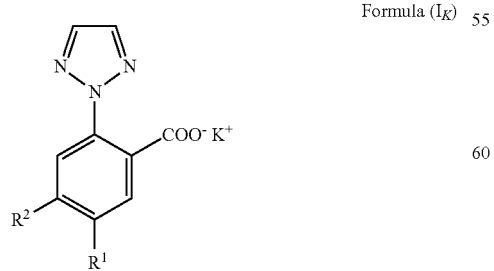

Formula ($I_K$)

wherein R¹ represents hydrogen and R² represents methyl; characterized by the presence of peaks in the X-ray powder diffraction diagram at the following angles of refraction 2θ: 5.4°, 10.7°, 16.1°, 21.6°, 27.0°; wherein said X-ray powder diffraction diagram is obtained by using combined Cu Kα1 and Kα2 radiation, without Kα2 stripping; and the accuracy of the 2θ values is in the range of 2θ+/−0.2°.

39. The crystalline form of the compound of Formula ($I_K$) according to claim 38, characterized by the presence of peaks in the X-ray powder diffraction diagram at the following angles of refraction 2θ: 5.4°, 8.8°, 10.7°, 12.0°, 16.1°, 21.6°, 23.3°, 24.2°, 27.0°, 32.6°; wherein said X-ray powder diffraction diagram is obtained by using combined Cu Kα1 and Kα2 radiation, without Kα2 stripping; and the accuracy of the 2θ values is in the range of 2θ+/−0.2°.

40. A crystalline form of the compound of Formula (I):

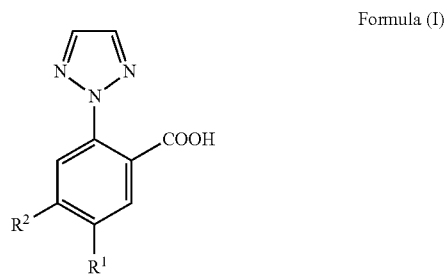

Formula (I)

wherein R¹ represents methoxy and R² represents hydrogen; characterized by the presence of peaks in the X-ray powder diffraction diagram at the following angles of refraction 2θ: 5.7°, 11.5°, 17.2°, 21.3°, 25.0°; wherein said X-ray powder diffraction diagram is obtained by using combined Cu Kα1 and Kα2 radiation, without Kα2 stripping; and the accuracy of the 2θ values is in the range of 2θ+/−0.2°.

41. The crystalline form of the compound of Formula (I) according to claim 40;
characterized by the presence of peaks in the X-ray powder diffraction diagram at the following angles of refraction 2θ: 5.7°, 11.5°, 16.0°, 17.2°, 18.9°, 19.7°, 21.3°, 23.7°, 25.0°, 27.9°; wherein said X-ray powder diffraction diagram is obtained by using combined Cu Kα1 and Kα2 radiation, without Kα2 stripping; and the accuracy of the 2θ values is in the range of 2θ+/−0.2°.

42. The crystalline form of the compound of Formula (I) according to claim 40; which has a melting point of about 80° C. as determined by differential scanning calorimetry.

43. The crystalline form of the compound of Formula (I) according to claim 41; which has a melting point of about 80° C. as determined by differential scanning calorimetry.

44. A crystalline form of the compound of Formula (I):

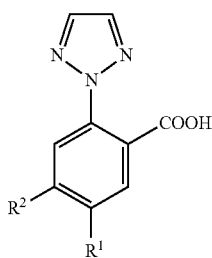

Formula (I)

wherein R¹ represents methoxy and R² represents hydrogen; characterized by the presence of peaks in the X-ray powder diffraction diagram at the following angles of refraction 2θ: 11.4°, 12.3°, 15.5°, 21.3°, 23.6°; wherein said X-ray powder diffraction diagram is obtained by using combined Cu Kα1 and Kα2 radiation, without Kα2 stripping; and the accuracy of the 2θ values is in the range of 2θ+/−0.2°.

45. The crystalline form of the compound of Formula (I) according to claim 44; characterized by the presence of peaks in the X-ray powder diffraction diagram at the following angles of refraction 2θ: 11.4°, 12.3°, 14.6°, 15.5°, 21.3°, 23.1°, 23.6°, 24.8°, 25.6°, 29.9°; wherein said X-ray powder diffraction diagram is obtained by using combined Cu Kα1 and Kα2 radiation, without Kα2 stripping; and the accuracy of the 2θ values is in the range of 2θ+/−0.2°.

46. The crystalline form of the compound of Formula (I) according to claim 44; which has a melting point of about 130-131° C. as determined by differential scanning calorimetry.

47. The crystalline form of the compound of Formula (I) according to claim 45; which has a melting point of about 130-131° C. as determined by differential scanning calorimetry.

48. A crystalline form of the compound of Formula (I):

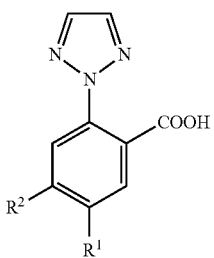

Formula (I)

wherein R¹ represents hydrogen and R² represents methyl; characterized by the presence of peaks in the X-ray powder diffraction diagram at the following angles of refraction 2θ: 6.2°, 12.5°, 15.1°, 18.8°, 25.2°; wherein said X-ray powder diffraction diagram is obtained by using combined Cu Kα1 and Kα2 radiation, without Kα2 stripping; and the accuracy of the 2θ values is in the range of 2θ+/−0.2°.

49. The crystalline form of the compound of Formula (I) according to claim 48; characterized by the presence of peaks in the X-ray powder diffraction diagram at the following angles of refraction 2θ: 6.2°, 11.3°, 12.5°, 13.3°, 15.1°, 17.0°, 17.8°, 18.8°, 22.6°, 25.2°; wherein said X-ray powder diffraction diagram is obtained by using combined Cu Kα1 and Kα2 radiation, without Kα2 stripping; and the accuracy of the 2θ values is in the range of 2θ+/−0.2°.

50. The crystalline form of the compound of Formula (I) according to claim 48; which has a melting point of about 125° C. as determined by differential scanning calorimetry.

51. The crystalline form of the compound of Formula (I) according to claim 49; which has a melting point of about 125° C. as determined by differential scanning calorimetry.

* * * * *